United States Patent
Westbrook

(10) Patent No.: US 9,873,728 B2
(45) Date of Patent: Jan. 23, 2018

(54) P75NTR(NBP) FUSION PROTEINS AND USE OF TREATING SYMPTOMS OF PAIN

(71) Applicant: Levicept Ltd., London (GB)

(72) Inventor: Simon Westbrook, London (GB)

(73) Assignee: LEVICEPT LTD., London (GB)

( * ) Notice: Subject to any disclaimer, the term of this patent is extended or adjusted under 35 U.S.C. 154(b) by 0 days.

(21) Appl. No.: 15/022,505

(22) PCT Filed: Sep. 18, 2014

(86) PCT No.: PCT/GB2014/052833
§ 371 (c)(1),
(2) Date: Mar. 16, 2016

(87) PCT Pub. No.: WO2015/040398
PCT Pub. Date: Mar. 26, 2015

(65) Prior Publication Data
US 2016/0222082 A1    Aug. 4, 2016

(30) Foreign Application Priority Data
Sep. 18, 2013  (GB) .................... 1316592.3

(51) Int. Cl.
| | | |
|---|---|---|
| *A61K 38/00* | (2006.01) | |
| *G01N 33/53* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 14/00* | (2006.01) | |
| *A61K 39/395* | (2006.01) | |
| *A61K 39/00* | (2006.01) | |
| *C07K 14/705* | (2006.01) | |

(52) U.S. Cl.
CPC ........ *C07K 14/70578* (2013.01); *A61K 38/00* (2013.01); *C07K 2317/52* (2013.01); *C07K 2319/30* (2013.01)

(58) Field of Classification Search
CPC .............. A61K 39/395; A61K 2300/00; A61K 2039/505; A61K 38/17; A61K 38/00; C07K 2319/30; C07K 2319/00; C07K 14/001; C07K 14/70578; C07K 2319/50; C07K 2317/569; C07K 2317/52; C07K 2317/56; C07K 2317/622; C07K 16/2803; C07K 16/2896; C07K 2317/21; C07K 2317/34; C07K 2317/41; C07K 2317/50; C07K 2317/53; C07K 2317/565; C07K 2317/73; C07K 2317/92; C07K 2317/94; C07K 2319/02; C07K 2319/33
See application file for complete search history.

(56) References Cited

U.S. PATENT DOCUMENTS

| 8,669,350 B2 * | 3/2014 | Chou ..................... C07K 16/40 424/134.1 |
| 2007/0243132 A1 * | 10/2007 | Russell-Jones ...... A61K 9/0014 424/1.11 |
| 2009/0232808 A1 * | 9/2009 | Priest ................... A61K 38/191 424/134.1 |
| 2013/0164286 A1 * | 6/2013 | Chou ..................... C07K 16/40 424/134.1 |

FOREIGN PATENT DOCUMENTS

| CN | 102233128 B | | 4/2013 | |
| WO | WO2006079176 | * | 8/2006 | ........... C07K 14/525 |
| WO | 2012101664 A1 | | 8/2012 | |
| WO | 2013136078 A2 | | 9/2013 | |
| WO | 2015040398 A1 | | 3/2015 | |
| WO | 2015040398 A3 | | 3/2015 | |

OTHER PUBLICATIONS

Pawson et al. 2003, Science 300:445-452.*
Burgess et al. J of Cell Bio. 1990, 111:2129-2138.*
Bowie et al. Science, 1990, 247:1306-1310.*
CN102233128 English version.*
Guo J. et al., 2013, proNGF inhibits proliferation and oligodendrogenesis of postnatal hippocampal neural stem/progenitor cells through p75NTR in vitro, Stem Cell Research, vol. 11(2), pp. 874-887.
Vilar M et al., Activation of the p75 neurotrophin receptor through conformational rearrangement of disulphide-linked receptor dimers, Neuron. Apr. 16, 2009;62(1):72-83.
Westbrook S., Fusion Protein, Levicept Ltd, WO2015040398A1, International Preliminary Report on Patentability Chapter 2, dated Sep. 18, 2015.
International Preliminary Report on Patentability, PCT/GB2014/052833, dated Sep. 18, 2015.
EPO Preliminary Response and Claims Amendment, PCT/GB2014/052833, dated Jul. 20, 2015.

* cited by examiner

*Primary Examiner* — Chang-Yu Wang
(74) *Attorney, Agent, or Firm* — Dennis A. Bennett; Chris Marion

(57) ABSTRACT

The present invention relates to a p75NTR neurotrophin binding protein(NBP)-Fc fusion protein comprising a p75NTR(NBP) portion and an immunoglobulin portion. In certain embodiments, the p75NTR(NBP)-Fc fusion protein is for use in the treatment of pain and/or a symptom of pain.

7 Claims, 5 Drawing Sheets

KEACPTGLYTHSGECCKACNLGEGVAQPCGANQTVCEPCLDSVTFSDVVSATEPCKPCTECV
GLQSMSAPCVEADDAVCRCAYGYYQDETTGRCEACRVCEAGSGLVFSCQDKQNTVCEECP
DGTYSDEANIVDPCLPCTVCEDTERQLRECTRWADAECEEIPGRWITRSTPEGSDSTAPSTQ
EPEAPPEQDLLIASTVAGVVTVMGSSQPVVIRGTIDNDIEGRMID*PKSCDK*THTCPPCPAPEL*
*LGGPSVFLFPPKPKDTLMISRTPEVTCVVVDVSHEDPEVKFNWYVDGVEVHNAKTKPREEQYNST*
*YRVVSVLTVLHQDWLNGKEYKCKVSNKALPAPIEKTISKAKGQPREPQVYTLPPSRDELTKNQVSLT*
*CLVKGFYPSDIAVEWESNGQPENNYKTTPPVLDSDGSFFLYSKLTVDKSRWQQGNVFSCSVMHEA*
*LHNHYTQKSLSLSPGK*

FIG. 1

KEACPTGLYTHSGECCKACNLGEGVAQPCGANQTVCEPCLDSVTFSDVVSATEPCKPCTECV
GLQSMSAPCVEADDAVCRCAYGYYQDETTGRCEACRVCEAGSGLVFSCQDKQNTVCEECP
DGTYSDEANHVDPCLPCTVCEDTERQLRECTRWADAECEEIPGRWTRSTPPEGSDSTAPSTQ
EPEAPPEQDLIASTVAGVVTTVMGGGEPKSSDKTHICPPCPAPELLGGPSVFLFPPKPKDTLM
ISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPG

FIG. 2

| | | |
|---|---|---|
| p75NTR | LASTVAGVVTTVMGSSQPVVTRGTTDNLIPVYCSILAAVVVGLVAYIAFKR | (SEQ ID 6) |
| Commercial p75-Fc | LASTVAGVVTTVMGIPKVDKKV-EPKSCDKTHTCPPCPAPELLGGPSVFLF | (SEQ ID 7) |
| p75-Fc | LASTVAGVVTTVMGIPKVDKKV-EPKSCDKTHTCPPCPAPELLGGPSVFLF | (SEQ ID 8) |
| p75-Fc C222S | LASTVAGVVTTVMGIPKVDKKV-EPKSSDKTHTCPPCPAPELLGGPSVFLF | (SEQ ID 9) |
| p75-Fc G4x1 | LASTVAGVVTTVMGGGG------EPKSSDKTHTCPPCPAPELLGGPSVFLF | (SEQ ID 10) |
| p75-Fc G4Sx1 | LASTVAGVVTTVMGGGGS-----EPKSSDKTHTCPPCPAPELLGGPSVFLF | (SEQ ID 11) |
| p75-Fc G4Sx2 | LASTVAGVVTTVMGGGGSGGGGSEPKSSDKTHTCPPCPAPELLGGPSVFLF | (SEQ ID 12) |
| Lonza IgG1za | ----------------NTKVDKRVEPKSCDKTHTCPPCPAPELLGGPSVFLF | (SEQ ID 13) |

FIG. 3

KEACPTGLYTHSGECCKACNLGEGVAQPGCGANQTVCEPCLDSVTFSDVVSATEPCKPCTECVGLQSMSAPCVEAD
DAVCRCAYGYYQDETTGRCEACRVCEAGSGLVFSCQDKQNTVCEECPDGTYSDEANHVDPCLPCTVCEDTERQLR
ECTRWADAECEEIPGRWITRSTPPEGGGEPKSSDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPAPIEKTISK
AKGQPREPQVVTLPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPG

FIG. 5

SEQUENCE LISTING

<160> NUMBER OF SEQ ID NOS: 15

<210> SEQ ID NO 1
<211> LENGTH: 460
<212> TYPE: PRT
<213> ORGANISM: Artificial Sequence
<220> FEATURE:
<223> OTHER INFORMATION: Fusion Protein

<400> SEQUENCE: 1

```
Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
        195                 200                 205

Gly Ser Ser Gln Pro Val Val Thr Arg Gly Thr Thr Asp Asn Asp Ile
210                 215                 220

Glu Gly Arg Met Asp Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400
```

```
Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 2
<211> LENGTH: 462
<212> TYPE: PRT
<213> ORGANISM: Artificial Sequence
<220> FEATURE:
<223> OTHER INFORMATION: Fusion Protein

<400> SEQUENCE: 2

Met Glu Trp Ser Trp Val Phe Leu Phe Phe Leu Ser Val Thr Thr Gly
1               5                   10                  15

Val His Ser Lys Glu Ala Cys Pro Thr Gly Leu Tyr Thr His Ser Gly
            20                  25                  30

Glu Cys Cys Lys Ala Cys Asn Leu Gly Glu Gly Val Ala Gln Pro Cys
        35                  40                  45

Gly Ala Asn Gln Thr Val Cys Glu Pro Cys Leu Asp Ser Val Thr Phe
    50                  55                  60

Ser Asp Val Val Ser Ala Thr Glu Pro Cys Lys Pro Cys Thr Glu Cys
65                  70                  75                  80

Val Gly Leu Gln Ser Met Ser Ala Pro Cys Val Glu Ala Asp Asp Ala
                85                  90                  95

Val Cys Arg Cys Ala Tyr Gly Tyr Tyr Gln Asp Glu Thr Thr Gly Arg
            100                 105                 110

Cys Glu Ala Cys Arg Val Cys Glu Ala Gly Ser Gly Leu Val Phe Ser
        115                 120                 125

Cys Gln Asp Lys Gln Asn Thr Val Cys Glu Glu Cys Pro Asp Gly Thr
    130                 135                 140

Tyr Ser Asp Glu Ala Asn His Val Asp Pro Cys Leu Pro Cys Thr Val
145                 150                 155                 160

Cys Glu Asp Thr Glu Arg Gln Leu Arg Glu Cys Thr Arg Trp Ala Asp
                165                 170                 175

Ala Glu Cys Glu Glu Ile Pro Gly Arg Trp Ile Thr Arg Ser Thr Pro
            180                 185                 190

Pro Glu Gly Ser Asp Ser Thr Ala Pro Ser Thr Gln Glu Pro Glu Ala
        195                 200                 205

Pro Pro Glu Gln Asp Leu Ile Ala Ser Thr Val Ala Gly Val Val Thr
    210                 215                 220

Thr Val Met Gly Gly Gly Glu Pro Lys Ser Ser Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300
```

```
Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
            325                 330                 335

Cys Lys Val Ser Asn Lys Ala Leu Pro Ala Pro Ile Glu Lys Thr Ile
        340                 345                 350

Ser Lys Ala Lys Gly Gln Pro Arg Glu Pro Gln Val Tyr Thr Leu Pro
    355                 360                 365

Pro Ser Arg Asp Glu Leu Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Tyr Ser Lys Leu Thr Val Asp Lys Ser Arg
        420                 425                 430

Trp Gln Gln Gly Asn Val Phe Ser Cys Ser Val Met His Glu Ala Leu
    435                 440                 445

His Asn His Tyr Thr Gln Lys Ser Leu Ser Leu Ser Pro Gly
450                 455                 460

<210> SEQ ID NO 3
<211> LENGTH: 443
<212> TYPE: PRT
<213> ORGANISM: Artificial Sequence
<220> FEATURE:
<223> OTHER INFORMATION: Fusion protein

<400> SEQUENCE: 3

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
        195                 200                 205
```

```
Gly Gly Gly Gly Glu Pro Lys Ser Ser Asp Lys Thr His Thr Cys Pro
            210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 4
<211> LENGTH: 1411
<212> TYPE: DNA
<213> ORGANISM: Artificial Sequence
<220> FEATURE:
<223> OTHER INFORMATION: Cloning insert

<400> SEQUENCE: 4
aagcttgccg ccaccatgga atggtcctgg gtgttcctgt tcttcctgtc cgtgaccacc        60
ggcgtgcact ccaaagaggc ttgtcccacc ggcctgtaca cccactctgg cgagtgttgc       120
aaggcctgta acctgggaga aggcgtggcc cagccttgtg cgctaatcga cagtgtgc        180 gagccctgcc tggactccgt gaccttctcc gatgtggtgt ccgccaccga gccttgcaag       240
ccctgcacag agtgtgtggg cctgcagtcc atgtccgccc cttgcgtgga agccgacgac       300
gccgtgtgta gatgcgccta cggctactac caggacgaga caaccggcag atgcgaggcc       360
tgcagagtgt gcgaagctgg ctctggcctg gtgttcagtt gtcaagacaa gcagaacacc       420
gtgtgcgagg aatgccccga cggcacctac tctgacgagg ccaatcacgt ggaccctgc        480 ctgccttgca ccgtgtgtga agataccgag cggcagctgc gcgagtgcac cagatgggct       540
gatgccgagt gcgaagagat ccctggccgg tggatcacca gatccacccc tccagagggc       600
tccgactcta ccgctcccct cacccaggaa cctgaggccc ctcctgagca ggacctgatc       660
gcttctacag tggccggcgt cgtgaccaca gtgatgggcg aggcggcga gcctaagtcc        720
```

-continued

```
tccgacaaga cccacacctg tcccccttgt cctgccccctg aactgctggg cggaccttcc      780
gtgtttctgt tcccccaaa gcccaaggac accctgatga tctcccggac ccccgaagtg      840
acctgcgtgg tggtggatgt gtcccacgag gaccctgaag tgaagttcaa ttggtacgtg      900
gacggcgtgg aagtgcacaa cgccaagacc aagcccagag aggaacagta caactccacc      960
taccgggtgg tgtctgtgct gaccgtgctg caccaggact ggctgaacgg caaagagtac     1020
aagtgcaagg tgtccaacaa ggccctgcca gcccccatcg aaaagaccat ctccaaggcc     1080
aagggccagc ccgggaacc ccaggtgtac acactgcccc ctagcaggga cgagctgacc     1140
aagaaccagg tgtccctgac ctgtctcgtg aagggcttct acccctccga tatcgccgtg     1200
gaatgggagt ccaacggcca gcctgagaac aactacaaga ccaccccccc tgtgctggac     1260
agcgacggct cattctttct gtactccaag ctgacagtgg acaagtcccg gtggcagcag     1320
ggcaacgtgt tctcctgcag cgtgatgcac gaggctctgc acaaccacta cacccagaag     1380
tccctgtccc tgagccccgg ctgatgaatt c                                    1411
```

```
<210> SEQ ID NO 5
<211> LENGTH: 21
<212> TYPE: PRT
<213> ORGANISM: Artificial Sequence
<220> FEATURE:
<223> OTHER INFORMATION: Secretase site

<400> SEQUENCE: 5

Gly Ser Ser Gln Pro Val Val Thr Arg Gly Thr Thr Asp Asn Asp Ile
1               5                   10                  15

Glu Gly Arg Met Asp
            20

<210> SEQ ID NO 6
<211> LENGTH: 51
<212> TYPE: PRT
<213> ORGANISM: Artificial Sequence
<220> FEATURE:
<223> OTHER INFORMATION: Partial sequence for sequence alignment.

<400> SEQUENCE: 6

Ile Ala Ser Thr Val Ala Gly Val Val Thr Thr Val Met Gly Ser Ser
1               5                   10                  15

Gln Pro Val Val Thr Arg Gly Thr Thr Asp Asn Leu Ile Pro Val Tyr
            20                  25                  30

Cys Ser Ile Leu Ala Ala Val Val Val Gly Leu Val Ala Tyr Ile Ala
        35                  40                  45

Phe Lys Arg
    50

<210> SEQ ID NO 7
<211> LENGTH: 50
<212> TYPE: PRT
<213> ORGANISM: Artificial Sequence
<220> FEATURE:
<223> OTHER INFORMATION: Partial sequence for sequence alignment

<400> SEQUENCE: 7

Ile Ala Ser Thr Val Ala Gly Val Val Thr Thr Val Met Gly Ile Pro
1               5                   10                  15

Lys Val Asp Lys Lys Val Glu Pro Lys Ser Cys Asp Lys Thr His Thr
            20                  25                  30
```

```
Cys Pro Pro Cys Pro Ala Pro Glu Leu Leu Gly Gly Pro Ser Val Phe
        35                  40                  45

Leu Phe
    50

<210> SEQ ID NO 8
<211> LENGTH: 50
<212> TYPE: PRT
<213> ORGANISM: Artificial Sequence
<220> FEATURE:
<223> OTHER INFORMATION: Partial sequence for sequence alignment

<400> SEQUENCE: 8

Ile Ala Ser Thr Val Ala Gly Val Val Thr Thr Val Met Gly Ile Pro
1               5                   10                  15

Lys Val Asp Lys Lys Val Glu Pro Lys Ser Cys Asp Lys Thr His Thr
            20                  25                  30

Cys Pro Pro Cys Pro Ala Pro Glu Leu Leu Gly Gly Pro Ser Val Phe
        35                  40                  45

Leu Phe
    50

<210> SEQ ID NO 9
<211> LENGTH: 50
<212> TYPE: PRT
<213> ORGANISM: Artificial Sequence
<220> FEATURE:
<223> OTHER INFORMATION: Partial sequence for sequence alignment

<400> SEQUENCE: 9

Ile Ala Ser Thr Val Ala Gly Val Val Thr Thr Val Met Gly Ile Pro
1               5                   10                  15

Lys Val Asp Lys Lys Val Glu Pro Lys Ser Ser Asp Lys Thr His Thr
            20                  25                  30

Cys Pro Pro Cys Pro Ala Pro Glu Leu Leu Gly Gly Pro Ser Val Phe
        35                  40                  45

Leu Phe
    50

<210> SEQ ID NO 10
<211> LENGTH: 45
<212> TYPE: PRT
<213> ORGANISM: Artificial Sequence
<220> FEATURE:
<223> OTHER INFORMATION: Partial sequence for sequence alignment

<400> SEQUENCE: 10

Ile Ala Ser Thr Val Ala Gly Val Val Thr Thr Val Met Gly Gly Gly
1               5                   10                  15

Gly Glu Pro Lys Ser Ser Asp Lys Thr His Thr Cys Pro Pro Cys Pro
            20                  25                  30

Ala Pro Glu Leu Leu Gly Gly Pro Ser Val Phe Leu Phe
        35                  40                  45

<210> SEQ ID NO 11
<211> LENGTH: 46
<212> TYPE: PRT
<213> ORGANISM: Artificial Sequence
<220> FEATURE:
<223> OTHER INFORMATION: Partial sequence for sequence alignment

<400> SEQUENCE: 11
```

```
Ile Ala Ser Thr Val Ala Gly Val Val Thr Val Met Gly Gly Gly
1               5                   10                  15

Gly Ser Glu Pro Lys Ser Ser Asp Lys Thr His Thr Cys Pro Pro Cys
            20                  25                  30

Pro Ala Pro Glu Leu Leu Gly Gly Pro Ser Val Phe Leu Phe
        35                  40                  45
```

<210> SEQ ID NO 12
<211> LENGTH: 51
<212> TYPE: PRT
<213> ORGANISM: Artificial Sequence
<220> FEATURE:
<223> OTHER INFORMATION: Partial sequence for sequence alignment

<400> SEQUENCE: 12

```
Ile Ala Ser Thr Val Ala Gly Val Val Thr Val Met Gly Gly Gly
1               5                   10                  15

Gly Ser Gly Gly Gly Gly Ser Glu Pro Lys Ser Ser Asp Lys Thr His
            20                  25                  30

Thr Cys Pro Pro Cys Pro Ala Pro Glu Leu Leu Gly Pro Ser Val
        35                  40                  45

Phe Leu Phe
    50
```

<210> SEQ ID NO 13
<211> LENGTH: 36
<212> TYPE: PRT
<213> ORGANISM: Artificial Sequence
<220> FEATURE:
<223> OTHER INFORMATION: Partial sequence for sequence alignment

<400> SEQUENCE: 13

```
Asn Thr Lys Val Asp Lys Lys Val Glu Pro Lys Ser Cys Asp Lys Thr
1               5                   10                  15

His Thr Cys Pro Pro Cys Pro Ala Pro Glu Leu Leu Gly Gly Pro Ser
            20                  25                  30

Val Phe Leu Phe
        35
```

<210> SEQ ID NO 14
<211> LENGTH: 7
<212> TYPE: PRT
<213> ORGANISM: Artificial Sequence
<220> FEATURE:
<223> OTHER INFORMATION: Linker sequence

<400> SEQUENCE: 14

```
Ala Glu Ala Ala Ala Lys Ala
1               5
```

<210> SEQ ID NO 15
<211> LENGTH: 410
<212> TYPE: PRT
<213> ORGANISM: Artificial
<220> FEATURE:
<223> OTHER INFORMATION: Fusion Protein

<400> SEQUENCE: 15

```
Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30
```

```
Gln Thr Val Cys Glu Pro Cys Leu Asp Ser Val Thr Phe Ser Asp Val
             35                  40                  45

Val Ser Ala Thr Glu Pro Cys Lys Pro Cys Thr Glu Cys Val Gly Leu
 50                  55                  60

Gln Ser Met Ser Ala Pro Cys Val Glu Ala Asp Asp Ala Val Cys Arg
 65                  70                  75                  80

Cys Ala Tyr Gly Tyr Tyr Gln Asp Glu Thr Thr Gly Arg Cys Glu Ala
                 85                  90                  95

Cys Arg Val Cys Glu Ala Gly Ser Gly Leu Val Phe Ser Cys Gln Asp
             100                 105                 110

Lys Gln Asn Thr Val Cys Glu Glu Cys Pro Asp Gly Thr Tyr Ser Asp
             115                 120                 125

Glu Ala Asn His Val Asp Pro Cys Leu Pro Cys Thr Val Cys Glu Asp
 130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                 165                 170                 175

Gly Gly Gly Glu Pro Lys Ser Ser Asp Lys Thr His Thr Cys Pro Pro
             180                 185                 190

Cys Pro Ala Pro Glu Leu Leu Gly Gly Pro Ser Val Phe Leu Phe Pro
             195                 200                 205

Pro Lys Pro Lys Asp Thr Leu Met Ile Ser Arg Thr Pro Glu Val Thr
     210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                 245                 250                 255

Glu Glu Gln Tyr Asn Ser Thr Tyr Arg Val Val Ser Val Leu Thr Val
             260                 265                 270

Leu His Gln Asp Trp Leu Asn Gly Lys Glu Tyr Lys Cys Lys Val Ser
             275                 280                 285

Asn Lys Ala Leu Pro Ala Pro Ile Glu Lys Thr Ile Ser Lys Ala Lys
 290                 295                 300

Gly Gln Pro Arg Glu Pro Gln Val Tyr Thr Leu Pro Pro Ser Arg Asp
305                 310                 315                 320

Glu Leu Thr Lys Asn Gln Val Ser Leu Thr Cys Leu Val Lys Gly Phe
                 325                 330                 335

Tyr Pro Ser Asp Ile Ala Val Glu Trp Glu Ser Asn Gly Gln Pro Glu
             340                 345                 350

Asn Asn Tyr Lys Thr Thr Pro Pro Val Leu Asp Ser Asp Gly Ser Phe
             355                 360                 365

Phe Leu Tyr Ser Lys Leu Thr Val Asp Lys Ser Arg Trp Gln Gln Gly
 370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly
                 405                 410
```

P75NTR(NBP) FUSION PROTEINS AND USE OF TREATING SYMPTOMS OF PAIN

CROSS REFERENCE TO RELATED APPLICATIONS

This application is a U.S. national stage filing under 35 U.S.C. §371 of PCT International Application No. PCT/GB2014/052833, filed Sep. 18, 2014, which claims the benefit of priority to Great Britain Application No. 1316592.3 filed Sep. 18, 2013. Each of the above-referenced applications is expressly incorporated by reference herein its entirety.

BACKGROUND TO THE INVENTION

The neurotrophins, neurotrophic growth factor (NGF), brain-derived neurotrophic factor (BDNF), neurotrophin 3 (NT-3), and neurotrophin 4/5 (NT-4/5) act via four receptors: the low affinity p75 neutrophic receptor (p75NTR), and the high affinity tyrosine kinase receptors; TrkA, TrkB, and TrkC. The low affinity receptor p75NTR binds and is activated by all four neurotrophins and has been reported to function independently from the other receptors. However, the Trk receptors are more selectively activated i.e. NGF is the selective ligand for TrkA, BDNF the ligand for TrkB and NT-3, 4/5 the ligands for TrkC. In addition it has been reported, when p75NTR and Trk proteins are co-expressed, they form complexes, which alter the signaling of both receptors (Huang and Reichardt, 2003, Annu Rev Biochem. 72:609-42). Indeed, it has been suggested that p75NTR facilitates the selectivity of each of the neutrophins for their respective Trk receptor.

The p75NTR is a member of the tumor necrosis factor receptor superfamily (TNFR-SF) and was the first member of this superfamily to be characterized fully. The superfamily (encoded by some 30 genes in humans) is defined by ligand-binding domains consisting of one or more (typically four) repeats of a 40 amino acid cysteine-rich domain (CRD) that was first identified in p75NTR (Johnson et al., 1986 Cell 47:545-554; Radeke et al., 1987 Nature 325:593-597). In contrast, no sequence motif is shared by the intracellular domains of all TNFR-SF family members. Consequently, signaling mechanisms of TNFR-SF proteins vary significantly.

An unusual feature of p75NTR structure is the existence of a disulfide-linked p75NTR dimer, formed via cysteinyl residues within the transmembrane domains. This disulfide linkage is required for effective neurotrophin-dependent signaling by p75NTR and plays an important role in the formation of an intracellular and extracellular domain (Vilar et al., 2009 Neuron 62:72-83). Neurotrophins exist physiologically as noncovalently associated dimers (Bothwell and Shooter, 1977 J Biol Chem. 252(23):8532-6.) with a distribution half-life of approximately 5 min (Tria et al., 1994 Exp Neurol. 127(2):178-83). Neurotrophin-dependent p75NTR activation involves association of a neurotrophin dimer with CRDs 2-4 of the two extracellular domains of a p75NTR dimer (He and Garcia, 2004 Science 304:870-875). Recent studies support a model in which neurotrophin binding causes the two extracellular domains of p75NTR dimers to move closer together, forcing the intracellular domains to splay apart in a snail-tong-like motion centered on the disulfide bond and permitting association of the intracellular domains with the signaling adapter proteins, NRIF and TRAF6 (Vilar et al., 2009 J Cell Sci 122:3351-3357, Vilar et al., 2009 Neuron 62:72-83). Intra-transmembrane domain disulfide bonds, such as are present in p75NTR, have not been described previously in other TNFR-SF family members, or in any other membrane protein.

p75NTR undergoes sequential proteolytic cleavage by α-secretase and γ-secretase activities and matrix metalloproteinases (MMPs), releasing its intracellular domain (ICD) into the cytoplasm, in a manner analogous to the cleavage-dependent signaling pathway of Notch and β-amyloid precursor protein (Jung et al., 2003 J Biol Chem 278:42161-42169; Kanning et al., 2003 J Neuro-sci 23:5425-5436). Cytoplasmic release of the p75NTR ICD by this pathway promotes signaling by associated NRIF (Kenchappa et al., 2006 Neuron 50:219-232). The role of the extracellular domain of p75NTR, following the proteolytic cleavage by α-secretase and γ-secretase activities and MMPs isn't fully understood.

It has been documented that NGF and other neurotrophins (BDNF, NT-3 and NT-4/5) play a significant role in pathology for example pain due to osteoarthritis, pancreatitis, rheumatoid arthritis, psoriasis, pruritis and multiple sclerosis (Watanabe et al., 2008 J Neurosci Res. 86(16):3566-74; Raychaudhuri et al., 2011 Arthritis Rheum. 63(11):3243-52; Barthel et al., 2009 Arthritis Res Ther. 11(3):R82; Truzzi et al., 2011 Cell Death Differ. 18:948-58; McDonald et al., 2011 Curr Med Chem. 18:234-44; Yamaoka et al., 2007 J Dermatol Sci. 46(1):41-51). It was been demonstrated that selective antibodies to any of the neutrophins; either NGF or BDNF, NT-3 and NT-4/5 significantly reduce pain. Furthermore, antibodies directed to the neurotrophin receptors p75NTR Trk A, Trk B or Trk C have also been demonstrated to be efficacious in models of pain (Orita S et al., 2010 J Orthop Res. 28:1614-20; Svensson P et al., 2010 Pain. 148:473-80; Iwakura et al., 2010 J Hand Surg Am. 35:267-73; Cirilio et al., 2010 Cell Mol Neurobiol. 30:51-62; Pezet et al., 2010 Pain. 90:113-25; Hayashi et al., 2011 J Pain. 12:1059-68; Chu et al., 2011 Pain. 152:1832-7; Ueda et al., 2010 J Pharmacol Sci.; 112:438-43; Ghilardi et al., 2010 Bone. 48:389-98; Fukui et al., 2010 J Orthop Res. 2010; 28:279-83). Fukui et al., (2010) in a model of pain (mechanical allodynia following sciatic nerve crush) demonstrated significant efficacy on pain related endpoints following treatment with an anti-p75NTR antibody. It was concluded from this study that the treatment with a p75NTR inhibitory antibody reduced CGRP and p75NTR expression resulting in a significant reduction in pain.

The current invention relates to a p75NTR neurotrophin binding protein (NBP)-Fc fusion protein. We describe the affinity and in vivo kinetics of such a molecule, as well as efficacy in the treatment of pain in an animal model. The p75NTR(NBP)-Fc fusion protein finds use in the treatment of pain and other neurotrophic factor related pathologies such as psoriasis, eczema, rheumatoid arthritis, cystitis, endometriosis and osteoarthritis.

BRIEF DESCRIPTION OF THE INVENTION

According to a first aspect of the present invention there is provided a p75NTR neurotrophin binding protein (NBP)-Fc fusion protein, comprising:
(a) a p75NTR(NBP) portion; and
(b) an immunoglobulin Fc portion.

Preferably, the p75NTR(NBP) and Fc portions are connected via a linker. More preferably, the linker comprises a peptide of formula $G_x$, where x is 1, 2, 3, 4, 5 or 6.

In a particularly preferred embodiment of the p75NTR (NBP)-Fc fusion protein according to the invention, the p75NTR(NBP) is a human p75NTR(NBP). In another particularly preferred embodiment of the p75NTR(NBP)-Fc fusion protein according to the invention, the Fc is a human Fc.

In yet another preferred embodiment, the p75NTR(NBP)-Fc fusion protein of the invention comprises or consists of the amino acid sequence set forth in SEQ ID NO. 3. In another preferred embodiment, the p75NTR(NBP)-Fc fusion protein of the invention comprises or consists of the amino acid sequence set forth in SEQ ID No. 15.

In a preferred embodiment, the p75NTR(NBP)-Fc fusion protein according to the invention binds to any of NGF, BDNF, NT3 or NT4/5 with a binding affinity ($K_d$) of between about 0.01 nM to about 50 nM as measured by surface plasmon resonance at 20° C.

In second aspect of the present invention, the p75NTR (NBP)-Fc fusion protein as described according to any other aspect of the invention is provided for use in the treatment of pain or a symptom of pain.

In a third aspect of the present invention, there is provided a nucleic acid molecule encoding the p75NTR(NBP)-Fc fusion protein according to the first or second aspects of the invention, optionally further comprising encoding a signal sequence.

In a fourth aspect of the present invention, there is provided a replicable expression vector for transfecting a cell, optionally a mammalian cell, the vector comprising the nucleic acid molecule according to the third aspect of the present invention.

Preferably, the replicable expression vector is a viral vector.

In a fifth aspect of the present invention, there is provided a host cell harbouring the nucleic acid molecule of the third aspect of the invention.

In a sixth aspect of the present invention, the nucleic acid molecule according to the third aspect of the invention or the vector according to the fourth aspect of the present invention is for use in the treatment of pain or a symptom of pain.

Pain or symptoms of pain include but are not limited to: acute pain; chronic pain; inflammatory pain; nociceptive pain; neuropathic pain; hyperalgesia; allodynia; central pain; cancer pain; post-operative pain; visceral pain; musculoskeletal pain; heart or vascular pain; head pain including migraine; orofacial pain, including dental pain; and back pain. Treatment of pain includes, but is not limited to, preventing, ameliorating, controlling, reducing incidence of, or delaying the development or progression of pain and/or a symptom of pain.

In a seventh aspect, there is provided the p75NTR(NBP)-Fc fusion protein according to the first or second aspects, or the nucleic acid or vector according to the third or fourth aspect, wherein the p75NTR(NBP)-Fc fusion protein or nucleic acid molecule or vector is for separate, sequential or simultaneous use in a combination combined with a second pharmacologically active compound.

In an eighth aspect, the present invention provides a pharmaceutical composition, comprising the p75NTR (NBP)-Fc fusion protein according to any aspect of the invention or the nucleic acid molecule or vector according to any aspect of the invention, and a pharmaceutically acceptable carrier and/or an excipient.

Preferably, the pharmaceutical composition is for use in any one or more of preventing, ameliorating, controlling, reducing incidence of, or delaying the development or progression of pain and/or a symptom of pain.

In a further aspect of the present invention, there is provided a kit comprising:

(a) the p75NTR(NBP)-Fc fusion protein according to any aspect of the present invention, or the nucleic acid molecule or vector according any aspect of the present invention, or the pharmaceutical composition according to the eighth aspect; and (b) instructions for the administration of an effective amount of said the p75NTR(NBP)-Fc fusion protein, nucleic acid molecule, vector or pharmaceutical composition to an individual for any one or more of the prevention or treatment of pain and/or a symptom of pain or for ameliorating, controlling, reducing incidence of, or delaying the development or progression of pain and/or a symptom of pain.

In yet another aspect of the present invention there is provided a method of treating and or preventing pain and or a symptom of pain in an individual comprising administering to said individual a therapeutically effective amount of the p75NTR(NBP)-Fc fusion protein according to any aspect of the invention, or the nucleic acid molecule or vector according to any aspect of the invention, optionally further comprising a pharmaceutically acceptable carrier, or the pharmaceutical composition according to the eighth aspect of the invention.

DESCRIPTION OF THE FIGURES

FIG. 1. Amino acid sequence of a p75NTR(NBP)-Fc fusion protein according to the present invention (SEQ ID No. 1). The alpha and gamma secretase cleavage sites are shown in bold type. The IgG 1 Fc portion is shown in italics.

FIG. 2. Amino acid sequence of a preferred p75NTR (NBP)-Fc fusion protein according to the present invention (SEQ ID No. 3). The IgG 1 Fc portion is shown in italics. The linker sequence between the p75NTR(NBP) and Fc portions is shown underlined.

FIG. 3. p75-NTR(NBP)-Fc fusion protein variants: 1: p75 NTR—The p75-NTR sequence (SEQ ID No. 6); 2: Commercially available p75-NTR-Fc fusion protein (SEQ ID No. 7); 3: p75_Fc—The commercially available p75-NTR-Fc fusion protein with the Fc sequence modified to that of the Lonza constant region of IgG1za (SEQ ID No. 8); 4: p75_Fc_C222S—The commercially available p75-NTR-Fc fusion protein with the Fc sequence modified to that of the Lonza constant region of IgG1za and an additional cysteine to serine mutation at position 222 (SEQ ID No. 9); 5: p75 Fc_G4x1—Variant 1, a proposed p75-NTR-Fc fusion protein with a four residue glycine linker (SEQ ID No. 10); 6: p75 Fc_G4Sx1—variant 2, a proposed p75-NTR-Fc fusion protein with a single tetra-glycine serine linker (SEQ ID No. 11); 7: p75_Fc_G4Sx2—variant 3, a proposed p75-NTR-Fc fusion protein with two tetra-glycine serine linkers (SEQ ID No. 12); 8: Lonza constant region of IgG1za (SEQ ID No. 13).

Figure 4:
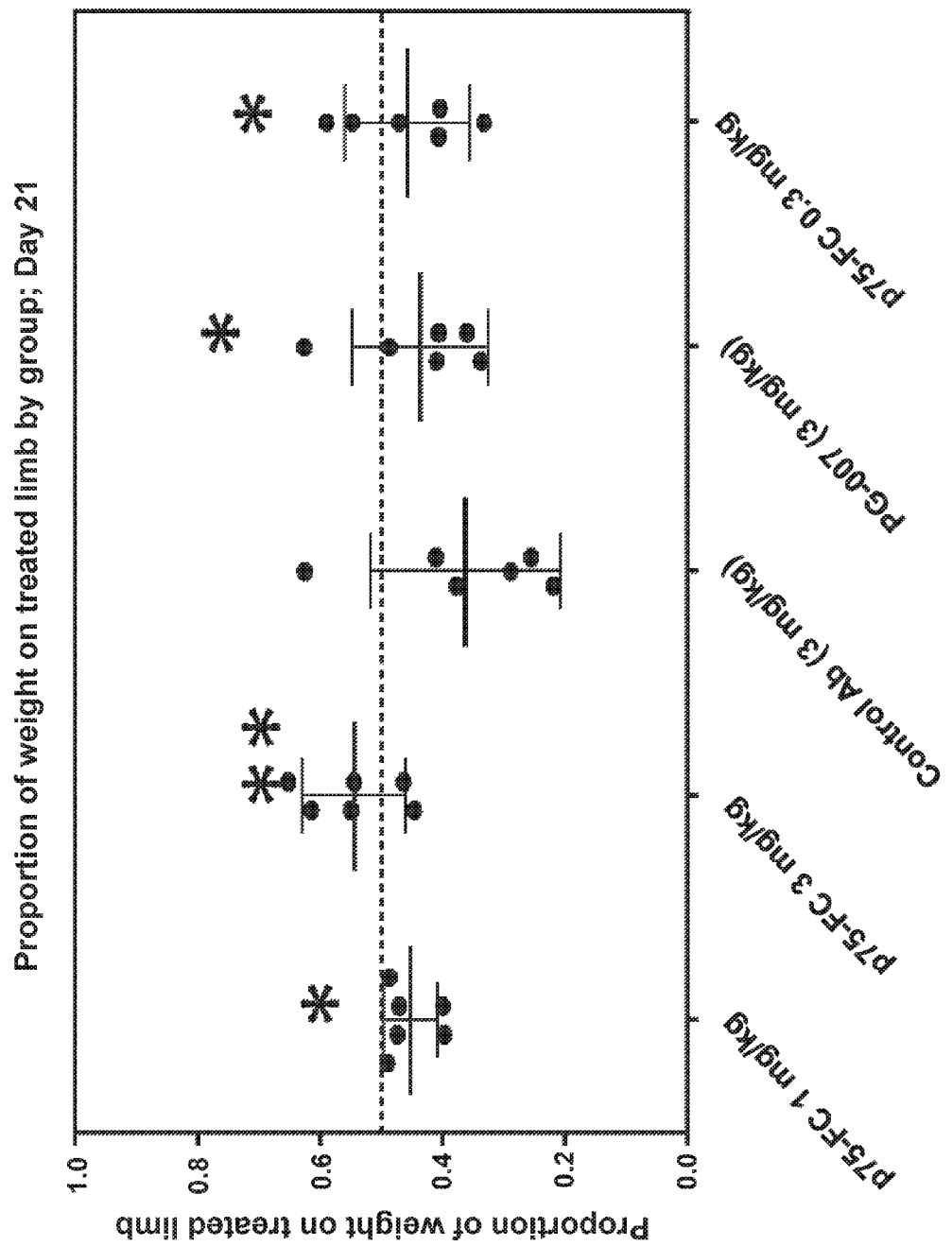

In this alignment a formatting scheme is used to highlight regions of similarity between the putative receptors, the Fc-fusion protein and the Fc constant region: Boxed type is used to indicate regions of identical sequence between the variant proteins and the p75-NTR; Single underlining is used to indicate regions of identical sequence between all of the Fc-fusion proteins and the Lonza IgG1za Fc; Italics are used to indicate linker regions at the junction of the p75-NTR and the Fc constant region; Double-underlining and bold type are used to indicate the position of non-identical sequence outside the linker region, at the position equivalent to 222 in the parental p75-NTR Fc-fusion protein.

FIG. 4. p75NTR-Fc significantly reduces pain in MIA-induced rodent model of OA. *P<O. 1 and **P<0.05.

FIG. 5. Amino acid sequence of a preferred p75NTR (NBP)-Fc fusion protein according to the present invention (SEQ ID No. 15). The IgG1 Fc portion is shown in italics. The linker sequence between the p75NTR(NBP) and Fc portions is shown underlined.

DETAILED DESCRIPTION OF THE INVENTION

According to a first aspect of the present invention there is provided a p75NTR neurotrophin binding protein (NBP)-Fc fusion protein, comprising:
(a) a p75NTR(NBP) portion; and
(b) an immunoglobulin Fc portion.

Preferably, the p75NTR(NBP) and Fc portions are connected via a linker. More preferably, the linker comprises a peptide of formula $G_x$, where x is 1, 2, 3, 4, 5 or 6.

In a particularly preferred embodiment of the p75NTR (NBP)-Fc fusion protein according to the invention, the p75NTR(NBP) is a human p75NTR(NBP). In another particularly preferred embodiment of the p75NTR(NBP)-Fc fusion protein according to the invention, the Fc is a human Fc.

In yet another preferred embodiment, the p75NTR(NBP)-Fc fusion protein of the invention comprises or consists of the amino acid sequence set forth in SEQ ID NO. 3. In another preferred embodiment, the p75NTR(NBP)-Fc fusion protein of the invention comprises or consists of the amino acid sequence set forth in SEQ ID No. 15.

Preferably the p75NTR neurotrophin binding protein, p75NTR(NBP), is pegylated, further preferably it is glycosylated.

The p75NTR(NBP)-Fc fusion protein of the present invention preferably binds to any one or more of NGF, BDNF, NT3 or NT4/5 with a binding affinity ($K_d$) of between about 0.01 nM to about 50 nM. In some preferred embodiments, the binding affinity ($K_d$) is between about 0.01 nM and any of about 0.1 nM, 0.2 nM, 0.5 nM, 1 nM, 1.5 nM, 2 nM, 2.5 nM, 3 nM, 3.5 nM, 4 nM, 4.5 nM, 5 nM, 5.5 nM, 6 nM, 6.5 nM, 7 nM, 7.5 nM, 8 nM, 8.5 nM, 9 nM, 9.5 nM, 10 nM, 15 nM, 20 nM, 25 nM, 30 nM, 35 nM, 40 nM, 45 nM or 50 nM as measured in an in vitro binding assay for NGF, BDNF, NT3 or NT4/5 such as described herein preferably as measured by surface plasmon resonance at 20° C. In some further preferred embodiments, binding affinity ($K_d$) is or is less than any of about 250 pM, 300 pM, 350 pM, 400 pM, 450 pM, 500 pM, 550 pM, 600 pM, 650 pM, 700 pM, 750 pM, 800 pM, 850 pM, 950 pM or 1 nM as measured in an in vitro binding assay for p75NTR(NBP)-Fc fusion protein with the neurotrophins such as described herein, preferably as measured by surface plasmon resonance at 20° C. In a further more preferred embodiment the binding affinity ($K_d$) is about 0.3 nM or about 1 nM, as measured in an in vitro binding assay for p75NTR(NBP)-Fc fusion protein with the neurotrophins such as described herein, preferably as measured by surface plasmon resonance at 20° C.

Preferably the p75NTR(NBP)-Fc fusion protein of the invention is for use in the treatment of pain or a symptom of pain. Without wishing to be bound by any particular theory, the inventors believe that the p75NTR(NBP)-Fc fusion protein achieves efficacy in the treatment of pain or a symptom of pain by effecting the functional activity of the aforementioned neurotrophins, (defined as modulating or up or down regulating the functional activity of the neurotrophins) NGF, BDNF, NT3 or NT4/5, for example the functional activity of the aforementioned neurotrophins resulting from their interaction with their respective receptors.

Preferably the p75NTR(NBP)-Fc fusion protein effects the functional activity of BDNF as assessed by functional assay of any of growth and differentiation of neurons and synapses, survival and differentiation in neuronal cell culture, Trk signalling, stimulation of axon outgrowth in vitro or in vivo.

Preferably the p75NTR(NBP)-Fc fusion protein effects the functional activity of NGF as assessed by measuring NGF binding to and activation of TrkA, as demonstrated in classical neuron survival assays (such as provided in Cowan et al. *Annu. Rev. Neurosci.* 2001; 24:551-600).

Preferably the p75NTR(NBP)-Fc fusion protein effects the functional activity of NT3 as assessed by measuring NT3 binding to and activation of endogenous Trk receptor activity, as demonstrated in Trk receptor phosphorylation, mitogen-activated protein kinase phosphorylation reporter assays or cell survival and neurite extension assays.

Preferably the p75NTR(NBP)-Fc fusion protein effects the functional activity of NT4/5 as assessed by measuring NT4/5 in vitro or in vivo phosphorylation and activation assays for example in myelin basic protein (MBP) phosphorylation assays or alternatively in vivo in a Matrigel angiogenesis assay of vascular endothelial growth factor (VEGF)/basic fibroblast growth factor-induced angiogenesis.

Preferably the p75NTR(NBP)-Fc fusion protein binds to the contact residues of one or more of the neurotrophins NGF, NT3, BDNF and NT4/5 as shown in He and Garcia (2001) Science, 301, pages 870-805.

Preferably the p75NTR(NBP)-Fc fusion protein is soluble, preferably soluble in aqueous solution, preferably soluble in a biological fluid such as serum, plasma, blood.

As used herein, the term, "Fc" or "immunoglobulin Fc" or "Ig Fc" is understood to mean the carboxyl-terminal portion of an immunoglobulin chain constant region, preferably an immunoglobulin heavy chain constant region, or a portion thereof. Preferably the immunoglobulin Fc comprises 1) a CH1 domain, a CH2 domain, and a CH3 domain, optionally with an immunoglobulin hinge region, 2) a CH1 domain and a CH2 domain, optionally with an immunoglobulin hinge region, 3) a CH1 domain and a CH3 domain, optionally with an immunoglobulin hinge region, 4) a CH2 domain and a CH3 domain, optionally with an immunoglobulin hinge region or 5) a combination of two or more domains selected from but not limited to CH1, CH2 and CH3 optionally combined with an immunoglobulin hinge region. Preferably the immunoglobulin Fc comprises at least an immunoglobulin hinge region, a CH2 domain and a CH3 domain, and optionally a CH1 domain. Preferably the immunoglobulin Fc comprises or consists of an Fc or a portion of an Fc of an immunoglobulin of isotype including but not limited to IgG, IgM, IgA, IgD, IgE, further preferably, IgG1, IgG2, IgG3, IgG4, IgA1, IgA2, sIgA, more preferably IgG1, IgG2 or IgG4, most preferably IgG1. Optionally the immunoglobulin Fc also comprises amino acid mutations, deletions, substitutions or chemical modifications which serve to minimise complement fixation or antibody-dependent cellular cytotoxicity or which improve affinity of binding to the Fc receptor.

Further preferably the immunoglobulin Fc comprises or consists of any of: (a) a CH2 domain or portion thereof and a CH3 domain or portion thereof, (b) a CH2 domain or portion thereof, or (c) a CH3 domain or portion thereof, wherein the immunoglobulin Fc or portion thereof is of isotype including but not limited to IgG, IgM, IgA, IgD, IgE, further preferably, IgG1, IgG2, IgG3, IgG4, IgA1, IgA2, sIgA, more preferably, IgG, IgG2 or IgG4, most preferably IgG1.

Preferably the immunoglobulin Fc comprises or consists of the carboxy terminal region of an immunoglobulin heavy chain and may comprise the CH2 and/or CH3 domains, or parts thereof, from IgG, IgA or IgD antibody isotypes, or the CH2 and/or CH3 and/or CH4 domains, or parts thereof from IgM or IgE. Preferably the immunoglobulin Fc comprises or consists of a fragment of the Fc, comprising mainly CH3 and a small portion of CH2, as is derivable by pepsin digestion of the immunoglobulin. Preferably the immunoglobulin Fc comprises or consists of the full Fc region, comprising CH2 and CH3, additionally connected to the hinge region which is a short segment of heavy chain connecting the CH1 and CH2 regions in the intact immunoglobulin, as may be produced by papain digestion of the immunoglobulin. Preferably the immunoglobulin hinge region comprises or consists of a hinge region or part of a hinge region derived from an IgG preferably human IgG, more preferably selected from but not limited to IgG1, IgG2, IgG3, or IgG4, most preferably IgG1 or is alternatively a species or allelic variant of the foregoing hinge region embodiments. The hinge region or a part of an immunoglobulin hinge region can be located at the C or N-terminal end of the Fc region, preferably at the N-terminal end.

According to a preferred embodiment of the present invention the immunoglobulin Fc preferably comprises or consists of an Fc or a portion of an Fc of an immunoglobulin which comprises one or more amino acid mutations of the wild type sequence in the CH2 region which reduce Fc effector function. Preferably these mutations are A330, P331 to S330, S331 (amino acid numbering with reference to the wildtype IgG1 sequence, wherein the CH2 region is in the human heavy chain IgG1 constant region: [Eur. J. Immunol. (1999) 29:2613-2624]. Preferably the immunoglobulin Fc is glycosylated and highly charged at physiological pH hence helping solubilise the p75NTR(NBP). The Fc region also permits detection of the p75NTR(NBP) by anti-Fc ELISA for example in diagnostic purposes. The p75NTR(NBP) of the invention is preferably synthesized in a cell which glycosylates the Ig Fc preferably at normal glycosylation sites.

Preferably the immunoglobulin Fc comprises or consists of a human immunoglobulin Fc region.

According to the present invention, the p75NTR(NBP)-Fc fusion protein preferably demonstrates advantageous biological properties of improved solubility of p75NTR(NBP) and/or stability of p75NTR(NBP) and/or improved serum half life p75NTR(NBP). Improved solubility is desirable in order that bioavailability of the p75NTR(NBP) is maximized on administration and accurate dosage of the p75NTR (NBP) can be determined and carried out. Improved solubility is advantageous to overcome the problem of aggregates which are undesirable causing pain in delivery in-vivo and leading to potential inflammation. Improved serum half life has the advantage of facilitating reduced levels or reduced frequency of dose requirement during use for treatment in order to achieve the equivalent or maintained therapeutic effect of the p75NTR(NBP) delivered. A prolonged half life and higher stability in blood or serum has the advantage of permitting a dosage regime of less frequent dosing and/or lower dosing levels hence reducing potential toxicity or side effects in-vivo. In this case the p75NTR (NBP)-Fc fusion protein is more potent in its therapeutic effect and/or more stable in the circulation. The resulting lower or less frequent doses are advantageous in minimising any potential toxic effects or side effects potentially associated with p75NTR(NBP) administration. The molecular weight of the p75NTR(NBP)-Fc fusion protein is also increased over p75NTR(NBP) alone, this has the advantage that the molecule will be well retained in the blood circulation when administered intravenously reducing the risk of penetration to undesired sites for example the central nervous system and making the molecule suitable for retention or concentration in the tissues targeted.

Preferably the p75NTR(NBP)-Fc fusion protein demonstrates improved solubility of p75NTR(NBP) and/or improved stability of p75NTR(NBP) and/or improved serum half life in comparison to p75NTR(NBP) alone. Preferably the improved solubility is solubility in an aqueous solution such as water preferably with excipients such as buffers and/or salts at preferably at a physiological pH, preferably at between pH 5 to pH 8, preferably about pH 7, or is solubility in a biological fluid such as serum or blood. Preferably the improved stability is stability of activity or structural integrity of the p75NTR(NBP) protein due to the effects of denaturation, oxidation, fragmentation or aggregation over a period of time, during a period storage or following freeze and thaw. Structural stability can be judged by standard measures of denaturation, oxidation, aggregation or aggregation, stability of activity can be measured by the binding or functional assays disclosed herein, methods of measuring protein serum half life are known.

Preferably the p75NTR(NBP)-Fc fusion protein can be expressed at high levels from variety of mammalian host cells to provide a single species and can be efficiently purified by affinity chromatography for example by binding to *Staphylococcus aureus* protein A. Preferably the p75NTR (NBP)-Fc fusion protein can dimerise and preferably the dimer has increased affinity to neurotrophins NGF, BDNF, NT3 or NT4/5 in comparison to p75NTR(NBP) alone. Tighter binding has the advantage of higher potency and a higher therapeutic efficacy as judged by the p75NTR(NBP) effects for example as determined by neurotrophin functional assays disclosed herein. Higher potency has the benefit that the p75NTR(NBP)-Fc fusion protein can be used at lower dosage amounts to achieve the same therapeutic efficacy hence reducing potential toxicity or side effects in-vivo.

Preferably the p75NTR(NBP)-Fc fusion protein of the invention has a half life in-vivo of about or more than any one of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 62, 164, 166, 168, 170, 172, 174, 176, 178, 180, 182, 184, 186, 188, 190, 192, 194, 196, 198, 200, 202, 204, 206, 208 or 210 hours+/−1 hour, further preferably the p75NTR(NBP)-Fc fusion protein of the invention has a half life in-vivo of about or more than 24 hours.

Further preferably the p75NTR(NBP)-Fc fusion protein of the invention has a half life in-vitro of about or more than any one of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 62, 164, 166, 168, 170, 172, 174, 176, 178, 180, 182, 184, 186, 188, 190, 192, 194, 196, 198, 200, 202, 204, 206, 208 or 210 days+/−1 day, further preferably the p75NTR(NBP)-Fc fusion protein of the invention has a half life in-vitro of about or more than 6 days. Preferably the stability is measured at about physiological pH, in a buffered aqueous solution, preferably at 20° C. or 37° C.

According to the foregoing preferred embodiments, preferably the in-vivo half life is half life in rat or half life in human, more preferably in human. Preferably the half life is determined from serum measurements of the levels of p75NTR(NBP)-Fc fusion protein of the invention following administration in-vivo for example by intravenous or subcutaneous injection.

The p75NTR(NBP) and immunoglobin Fc portions of the p75NTR(NBP)-Fc fusion protein may be connected by a linker. The linker preferably the linker comprises or consists of one or a plurality of amino acids or comprises or consists of a polypeptide sequence of amino acids, preferably about 1 to about 25 amino acids, preferably any one of 1, 2, 3, 4, 5, 6, 7, 8, or 9 amino acids further preferably any one of about 10, 11, 12, 13, 14, 15, 16, 17, 18, 19, 20, 21 22, 23 or 24 amino acids, most preferably 13 amino acids.

Preferably the linker comprises or consists of a polypeptide sequence of amino acids that lacks any stable secondary structure such as alpha helix, beta strand, $3_{10}$ helix and pi helix, polyproline helix, alpha sheet. Preferably the linker region comprises or consists of a polypeptide sequence of amino acids that defines a flexible or dynamic or unstructured polypeptide such as for example a flexible loop, random coil or flexible turn, such unstructured polypeptides are often found connecting regions of secondary structure in large protein molecules.

Preferably the linker is a polypeptide sequence of amino acids that comprises greater than or about 50% glycine and/or alanine and/or serine in p75NTR(NBP), further preferably greater than or about 55%, 60%, 65%, 70%, 75%, 80%, 85%, 90%, 95% or 100% glycine and/or alanine and/or serine in p75NTR(NBP). Preferably the linker region comprises or consists of a polypeptide sequence of amino acids that comprises both glycine and serine, preferably with a greater proportion of glycine that serine, preferably the linker region comprises or consists of flexible linkers.

Without wishing to be bound by any particular theory, the inventors believe that flexible linkers overcome or prevent steric hindrance which could interfere with the aforementioned neurotrophin binding ability or biological activity of the p75NTR(NBP)-Fc fusion when compared to p75NTR (NBP) alone. Hence the linker region preferably permits flexibility between the p75NTR(NBP) portion and the immunoglobin Fc portion and allows retention of or improvement of the aforementioned biological activity of p75NTR(NBP)-Fc fusion protein in comparison to free or native p75NTR(NBP) alone as determined by binding to neurotrophins using binding assays such as described herein.

Further preferably the linker is immunologically inert, such that it does not trigger complement mediated lysis, does not stimulate antibody-dependent cell mediated cytotoxicity (ADCC), does not activate microglia or T-cells. Preferably the linker region is reduced in one or more of these activities.

Further preferably the linker comprises or consists of a polypeptide known or predicted from structural analysis or structural prediction to be a flexible or dynamic or unstructured polypeptide or to lack a stable secondary structure.

Most preferably, the linker comprises or consists of a peptide of formula $G_x$, where x is 1, 2, 3, 4, 5 or 6.

The p75NTR(NBP)-Fc fusion protein of the invention may also comprise a proteolytic cleavage site, optionally interposed between the p75NTR(NBP) portion and the immunoglobin Fc portion. The proteolytic cleavage site may be located in the linker or at the junction of the linker with either the p75NTR(NBP) portion or/and the immunoglobin Fc portion. The p75NTR(NBP) may optionally be cleaved from the immunoglobin Fc portion prior to formulation and or administration for therapeutic purposes.

Alternatively, the p75NTR(NBP)-Fc fusion protein of the invention may be engineered to remove proteolytic cleavage sites. In a preferred embodiment, alpha and gamma secretase cleavage sites can be removed. In a particularly preferred embodiment, the sequence GSSQPVVTRGTTDNDI-EGRMD (SEQ ID No. 5) is removed.

In further preferred embodiments certain amino acids in the p75NTR(NBP)-Fc fusion protein may be changed in order to improve properties such as yield or solubility. One particularly preferred embodiment is the change of the cysteine residue at position 222 to a serine residue, which was found to reduce aggregation of the protein as it is expressed from CHO cells during manufacture of the protein.

Preferably the linker and/or the immunoglobin Fc portion do not impair or significantly impair the p75NTR(NBP) portion:
(a) effect on the functional activity of the neurotrophins (defined as modulating or up or down regulating the functional activity of the neurotrophins) NGF, BDNF, NT3 or NT4/5,
(b) binding affinity for any of NGF, BDNF, NT3 or NT4/5 with a binding affinity of between about 0.1 nM to about 50 nM
(c) ability to binds to each of the neurotrophins NGF, NT3, BDNF and NT4/5, preferably human NGF, NT3, BDNF and NT4/5.

According to another aspect of the invention there is provided a nucleic acid molecule encoding the p75NTR (NBP)-Fc fusion protein according to the first or second aspects. Preferably the nucleic acid molecule is for use in the treatment of pain.

According to a preferred embodiment of the present invention the nucleic acid molecule may further comprise a region encoding a signal sequence, preferably a p75NTR signal sequence for example a DNA or RNA sequence.

According to another aspect of the invention there is provided a replicable expression vector for transfecting a cell, the vector comprising the nucleic acid molecule of the third aspect, preferably the vector is a viral vector. Preferably the vector is for use in the treatment of pain.

Further according to the above aspects of the invention there is provided a method of expressing the nucleic acid molecule or the vector of the invention to produce or secrete the p75NTR(NBP)-Fc fusion protein. Preferably the method comprises the introduction of the nucleic acid molecule or vector into a cell and expression of the nucleic acid therein to produce or secrete the p75NTR(NBP)-Fc fusion protein. Preferably the nucleic acid molecule or vector is introduced into the cell in-vitro alternatively in-vivo. Preferably the expressed p75NTR(NBP)-Fc fusion protein is expressed in-vitro, optionally further isolated and purified, alternatively preferably the expressed p75NTR(NBP)-Fc fusion protein is expressed in-vivo, preferably the in-vivo expression constitutes gene therapy. Preferably the vector is a replicable expression vector, optionally for transfecting a mammalian cell, preferably the vector is a viral vector.

According to another aspect of the invention there is provided a host cell harbouring the nucleic acid molecule or vector of either the third or fourth aspect, preferably the cell is a mammalian cell.

According to another aspect of the invention there is provided the p75NTR(NBP)-Fc fusion protein for use in the treatment of pain or a symptom of pain, or a nucleic acid or vector for use in the treatment of pain or symptom of pain. Pain or symptom of pain may include but is not limited to:
(a) acute pain and/or spontaneous pain,
(b) chronic pain and or on-going pain,
(c) inflammatory pain including any one of arthritic pain, pain resulting from osteoarthritis or rheumatoid arthritis, resulting from inflammatory bowel diseases, psoriasis and eczema
(d) nociceptive pain,
(e) neuropathic pain, including painful diabetic neuropathy or pain associated with post-herpetic neuralgia,
(f) hyperalgesia,
(g) allodynia,
(h) central pain, central post-stroke pain, pain resulting from multiple sclerosis, pain resulting from spinal cord injury, or pain resulting from Parkinson's disease or epilepsy,
(i) cancer pain,
(j) post-operative pain,
(k) visceral pain, including digestive visceral pain and non-digestive visceral pain, pain due to gastrointestinal (GI) disorders, pain resulting from functional bowel disorders (FBD), pain resulting from inflammatory bowel diseases (IBD), pain resulting from dysmenorrhea, pelvic pain, cystitis, interstitial cystitis or pancreatitis,
(l) musculo-skeletal pain, myalgia, fibromyalgia, spondylitis, sero-negative (non-rheumatoid) arthropathies, non-articular rheumatism, dystrophinopathy, Glycogenolysis, polymyositis, pyomyositis,
(m) heart or vascular pain, pain due to angina, myocardial infarction, mitral stenosis, pericarditis, Raynaud's phenomenon, scleredoma, scleredoma or skeletal muscle ischemia,
(n) head pain including migraine, migraine with aura, migraine without aura cluster headache, tension-type headache.
(o) orofacial pain, including dental pain, temporomandibular myofascial pain or tinnitus, or
(p) back pain, bursitis, menstrual pain, migraine, referred pain, trigeminal neuralgia, hypersensitisation, pain resulting from spinal trauma and/or degeneration or stroke.

Treatment of pain includes, but is not limited to, preventing, ameliorating, controlling, reducing incidence of, or delaying the development or progression of pain and/or a symptom of pain.

According to another aspect of the invention there is provided the p75NTR(NBP)-Fc fusion protein according to the first or second aspect or the preferred embodiments thereof, or the nucleic acid molecule or vector according to the third and fourth aspects wherein the p75NTR(NBP)-Fc fusion protein or the nucleic acid molecule or vector is for separate, sequential or simultaneous use in a combination combined with a second pharmacologically active compound. Preferably the second pharmacologically active compound of the combination may include but is not limited to;

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1, 2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-$HT_{1B/1D}$ agonist such as eletriptan, sumatriptan, naratriptan, zolmitriptan or rizatriptan;

a 5-$HT_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentane carboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);

a sodium channel blocker, such as lidocaine; or a 5-HT3 antagonist, such as ondansetron;

and the pharmaceutically acceptable salts and solvates thereof.

According to a further aspect of the present invention there is provided a method of treating, preventing, ameliorating, controlling, reducing incidence of, or delaying the development or progression of pain or any of the foregoing pain and/or symptoms of pain in an individual, comprising administration to the individual of an effective amount of the p75NTR(NBP)-Fc fusion protein according to the first or second aspect or the preferred embodiments thereof, or the nucleic acid molecule or vector according to the third and fourth aspects.

The present invention is applicable in both human and veterinary medical fields. Preferably the individual is a mammal, for example a companion animal such as a horse, cat or dog or a farm animal such as a sheep, cow or pig. Most preferably the individual is a human.

According to an eighth aspect of the present invention there is provided a pharmaceutical composition for any one or more of treating, preventing, ameliorating, controlling, reducing incidence of, or delaying the development or progression of pain or any of the foregoing pain/or symptoms, comprising the p75NTR(NBP)-Fc fusion protein according to the first or second aspect or the preferred embodiments thereof, or the nucleic acid molecule or vector according to the third and fourth aspects and a pharmaceutically acceptable carrier and/or an excipient.

Preferably the p75NTR(NBP)-Fc fusion protein according to the first or second aspects or the preferred embodiments thereof, or the nucleic acid molecule or vector according to the third and fourth aspects or the pharmaceutical of the eighth aspect is prepared for or suitable for oral, sublingual, buccal, topical, rectal, inhalation, transdermal, subcutaneous, intravenous, intra-arterial, intramuscular, intracardiac, intraosseous, intradermal, intraperitoneal, transmucosal, vaginal, intravitreal, intra-articular, peri-articular, local or epicutaneous administration.

Preferably the p75NTR(NBP)-Fc fusion protein according to the first or second aspect or the preferred embodiments thereof, or the nucleic acid molecule or vector according to the third and fourth aspects or the pharmaceutical composition of the eighth aspect is prepared for or suitable for administration prior to and/or during and/or after the onset of pain or for such use.

Preferably the p75NTR(NBP)-Fc according to the first or second aspect or the preferred embodiments thereof, or the nucleic acid molecule or vector according to the third and fourth aspects or the pharmaceutical composition of the eighth aspect is for or prepared for administration between once to 7 times per week, further preferably between once to four times per month, further preferably between once to six times per 6 month period, further preferably once to twelve times per year. Preferably the medicament is to be or prepared to be peripherally administered in a period including but not limited to: once daily, once every two, three, four, five or six days, weekly, once every two weeks, once every three weeks, monthly, once every two months, once every three months, once every four months, once every five months, once every six months, once every seven months, once every eight months, once every nine months, once every ten months, once every eleven months or yearly.

Further preferably the p75NTR(NBP)-Fc fusion protein according to the first or second aspect or the preferred embodiments thereof, or the nucleic acid molecule or vector according to the third and fourth aspects or the pharmaceutical composition of the eighth aspect is to be or prepared to be peripherally administered via a route including but not limited to one or more of; orally, sublingually, buccally, topically, rectally, via inhalation, transdermally, subcutaneously, intravenously, intra-arterially or intramuscularly, via intracardiac administration, intraosseously, intradermally, intraperitoneally, transmucosally, vaginally, intravitreally, epicutaneously, intra-articularly, peri-articularly or locally.

Preferably the p75NTR(NBP)-Fc fusion protein according to the first or second aspect or the preferred embodiments thereof, or the nucleic acid molecule or vector according to the third and fourth aspects or the pharmaceutical composition of the eighth aspect is for or is prepared for administration at a concentration of between about 0.05 to about 200 mg/ml; preferably at any one of about 0.05, 0.1, 0.5, 1, 5, 10, 15, 20, 25, 30, 35, 40, 45, 50, 55, 60, 65, 70, 75, 80, 85, 90, 95, 100, 110, 120, 130, 140, 150, 160, 170, 180, 190 or 200 mg/ml+/−about 10% error, most preferably at about 3 mg/ml in veterinary applications and 0.1 in humans.

Preferably the p75NTR(NBP)-Fc fusion protein according to the first or second aspect or the preferred embodiments thereof, or the nucleic acid molecule or vector according to the third and fourth aspects or the pharmaceutical composition of the eighth aspect is for or is prepared for administration at a concentration of between about 0.1 to about 200 mg/kg of body weight; preferably at any one of about 0.5, 1, 5, 10, 15 20, 25, 30, 35, 40, 45, 50, 55, 60, 65, 70, 75, 80, 85, 90, 95, 100, 110, 120, 130, 140, 150, 160, 170, 180, 190 or about 200 mg/kg of body weight+/−about 10% error, most preferably at about 10 mg/kg in veterinary applications and 0.3 in humans According to a ninth aspect of the present invention there is provided a kit comprising:
(a) the p75NTR(NBP)-Fc fusion protein according to the first or second aspect or the preferred embodiments thereof, or the nucleic acid molecule or vector according to the third and fourth aspects or the pharmaceutical composition of the eighth aspect; and (b) instructions for the administration of an effective amount of said p75NTR(NBP)-Fc fusion protein, nucleic acid molecule, vector or pharmaceutical composition to an individual for any one or more of the prevention or treatment of pain and/or symptoms of pain or for ameliorating, controlling, reducing incidence of, or delaying the development or progression of pain and/or symptoms of pain.

The kit may include one or more containers containing the p75NTR(NBP)-Fc fusion protein, nucleic acid, vector or pharmaceutical composition described herein and instructions for use in accordance with any of the methods and uses of the invention. The kit may further comprise a description of selecting an individual suitable for treatment based on identifying whether that individual has a pain or a symptom of pain or is at risk of having such. The instructions for the administration of the pharmaceutical composition may include information as to dosage, dosing schedule and routes of administration for the intended treatment.

According to yet another aspect of the present invention there is provided the p75NTR(NBP)-Fc fusion protein according to the first or second aspect or the preferred embodiments thereof, or the nucleic acid molecule or vector according to the third and fourth aspects or the pharmaceutical composition of the eighth aspect for use in any one or more of the prevention or treatment or for ameliorating, controlling, reducing incidence of, or delaying the development or progression of a condition or the symptoms of a condition associated with any one or more of the neurotrophins NGF, BDNF, NT-3, NT-4/5.

NGF (Nerve growth factor) binds with at least two classes of receptors: the p75NTR and TrkA, a transmembrane tyrosine kinase, it is involved in axonal growth, branching and elongation. Conditions and symptoms associated with NGF are known. NGF is expressed in and associated with inflammatory conditions and pain [Protein Sequence NP_002497.2, NP_038637]. Also, NGF has been shown to play a role in number cardiovascular diseases, such as coronary atherosclerosis, obesity, type 2 diabetes, and metabolic syndrome as well as in Multiple Sclerosis. Reduced plasma levels of NGF (and also of BDNF) have been associated with acute coronary syndromes and metabolic syndromes. NGF is also related to various psychiatric disorders, such as dementia, depression, schizophrenia, autism, Rett syndrome, anorexia nervosa, and bulimia nervosa and has also been implicated in development of Alzheimer's disease and neurodegenerative disorders. NGF has also been shown to accelerate wound healing and there is evidence that it could be useful in the treatment of skin ulcers and corneal ulcers, it has been shown to reduce neural degeneration and to promote peripheral nerve regeneration in rats.

BDNF (brain-derived neurotrophic factor) is a neurotrophin which supports neuronal survival and growth during development of the nervous system [Protein Sequence NP_001137277.1, NP_001041604]. BDNF binds cell surface receptors TrkB and p75NTR and also modulates the activity of Alpha-7 nicotinic receptor. Conditions and symptoms associated with BDNF are known. BDNF has been shown to play a significant role in the transmission of physiologic and pathologic pain, particularly in models of acute pain, inflammatory pain and neuropathic pain, where BDNF synthesis is found to be greatly increased; also BDNF has been shown to be up-regulated in conditions of chronic pain as well as further conditions such as eczema and psoriasis. Down-regulation of BDNF is seen in depression, schizophrenia, obsessive-compulsive disorder, Alzheimer's disease, Huntington's disease, Rett syndrome, and dementia, as well as anorexia nervosa and bulimia nervosa.

Neurotrophin-4 (NT-4), also known as neurotrophin-5 (NT-5), is a neurotrophic factor that signals predominantly through the p75NTR and TrkB receptors and promotes the survival of peripheral sensory sympathetic neurons. The mature peptide of this protein is identical in all mammals examined including human, pig, rat and mouse. [Protein Sequence NP_006170, NP_937833]. NT-4 is synthesized by most neurons of the dorsal root ganglion (DRG) and those in the paravertebral and prevertebral sympathetic ganglia, spinal dorsal and ventral horn and is found expressed in many tissues including the prostate, thymus, placenta and skeletal muscle. Conditions and symptoms associated with NT-4/5 are known. Defects in NT4/5 are associated with susceptibility to primary open angle glaucoma. Neurotrophin 4 has also been shown to contribute to breast cancer cell survival and is a target to inhibit tumour growth. NT-4/5 is known to be involved in pain-signalling systems such as nociceptive pain, upregulation of NT-4/5 is also seen in chronic inflammatory conditions of the skin, such as dermatitis, eczema, prurigo lesions of atopic dermatitis. Down regulation of NT-4/5 is seen in Alzheimer's Disease, Huntington's disease.

Neurotrophin-3 (NT-3), is a neurotrophin that is structurally related to beta-NGF, BDNF, and NT-4, and that controls survival and differentiation of mammalian neurons and the maintenance of the adult nervous system, and may affect development of neurons in the embryo when it is expressed in human placenta. Conditions and symptoms associated with NT3 are known. NTF3-deficient mice generated by gene targeting display severe movement defects of the limbs. NT-3 signals through the Trk receptors and promotes the growth and survival of nerve and glial cells [Protein Sequence NP_001096124.1 and NP_032768]. The amino acid sequences of human, Mouse and rat NT-3 are identical. NT3 and its cognate receptor, tyrosine kinase C (TrkC), are known to modulate neuropathic pain and nociceptive pain and the mechanism of nociception and proporioception, for example NT3 expression is increased in the small DRG cells of neuropathic animals. NT3 expression is also associated with neuropathies such as diabetic polyneuropathy and HIV-related neuropathy, large fiber neuropathy including atrophy, it is further involved in the development of hyperalgesia (a decrease in the threshold of a normally noxious stimuli), allodynia (a non-noxious stimulus becomes noxious), and spontaneous pain (pain in the apparent absence stimuli) and is a known modulator of muscle pain.

The invention will now be described by reference to the following examples which are provided to illustrate, but not to limit, the invention.

EXAMPLES

In Silico Immunogenicity Testing for p75NTR-Fc Sequences

Recombinant DNA technology is currently utilised to produce a wide range of biopharmaceuticals, including the novel class of multi-functional therapeutic fusion proteins based on the Fc (fragment crystallisable) of monoclonal antibodies (mAbs) (Huang 2009 Curr Opin Biotechnol, 20(6), 692-9). The fusion of a therapeutic protein to an Fc domain enhances the overall therapeutic effect of the biopharmaceutical by extending the serum half-life of the molecule in two distinct ways. Firstly, recycling Fc-fusion by pH dependent binding to the neonatal Fc receptor (FcRn) reduces the degradation of the therapeutic protein in endosomes. Secondly, the increase in molecular size both through addition of the Fc-domains and by the Fc-mediated dimerization to the therapeutic protein helps limit renal clearance relative to the therapeutic molecule.

Fusion proteins can be created by directly joining two or more domains together. However, this may lead to undesirable molecular properties in the resulting fusion protein, such as impaired bio-activity (Bai et al. 2005 Proc. Natl. Acad. Sci. 102 7292-7296), protein misfolding (Zhao et al. 2008 Protein Expr. Purif. 61, 73-77) or low production yields (Amet et al. 2009 Pharm. Res. 26, 523-528). A linker sequence can be inserted between the domains to address these potential issues but several factors must be taken into consideration to choose the appropriate linker. Firstly, the linker must reflect the overall intended function of the domains within the fusion protein. In some situations the domains must operate independently, so linker flexibility is desirable. Conversely, a rigid linker may be required if the domains are to be tethered. Secondly, the linker must not introduce any unwanted functionality into the fusion protein, through post-translation modifications (PTMs). Lastly, the potential immunogenicity of the linker and the regions flanking the linker must be considered, as the linker may be a de novo designed sequence which does not occur naturally in the human body.

Most therapeutic proteins are, to a varying extent, immunogenic (Van Walle et al. 2007 Expert Opin Biol Ther. 7(3):405-18, Stas et al. 2009 Immunogenicity assessment of antibody therapeutics. Cambridge University Press, Cambridge) and even so called fully-human antibody therapeutics may contain immunogenic regions (Harding et al. 2010 MAbs. 2, 256-265). Immunogenicity is the ability to induce a Th (T-helper) response, which is triggered when a unique T-cell receptor recognizes a peptide bound to the HLA class II molecules displayed on antigen presenting cells. The peptides are generated from proteins internalized by the antigen presenting cell which are then processed through the endosomal cleavage pathway. Only peptides with sufficient affinity for the HLA class II molecules will be presented on the cell surface, and could possibly trigger a Th response.

Consequently, it is possible to lower the immunogenicity potential by removing Th epitopes, a process known as de-immunization (Chamberlain 2002 The Regulatory Review 5, 4-9, Baker and Jones 2007 Curr. Opin Drug Discov. Devel. 10, 219-227). This is achieved by predicting which peptides in the therapeutic protein can bind to HLA class II molecules, and subsequently introduce substitutions that eliminate or reduce the peptide binding affinity for HLA class II molecules.

There are several HLA class II genes and almost all are highly polymorphic. Additionally, HLA class II molecules consist of an alpha and beta chain, each derived from a different gene which, with the inherent polymorphism, further increases variation. Specifically, every individual expresses the genes: DRA/DRB, DQA/DQB and DPA/DPB. Of these only DRA is non-polymorphic. In addition, a 'second' DRB gene (DRB3, DRB4 or DRB5) may also be present, the product of which also associates with the DRA chain.

The focus during a de-immunization is on the DR allotypes, which are known to express at a higher level than DQ and DP (Laupeze et al. 1999 Hum. Immunol. 60, 591-597, Gansbacher and Zier 1988 Cell Immunol. 117, 22-34, Berdoz et al. 1987 J. Immunol. 139, 1336-1341, Stunz et al. 1989 J. Immunol. 143, 3081-3086). DR allotypes are usually referred to by the DRB gene as the DRA gene remains constant, for example DRB1*01:01, where the digits are allele-specific.

The assessment of severity for individual epitopes is based on the criteria of promiscuity, i.e. the number of HLA allotypes a specific epitope binds to, as well as the importance (frequency) of the allotypes in the population and a qualitative assessment of the HLA:peptide complex binding strength. As the T-cell population of an individual has been selected to not recognize 'self-peptides' it is possible to screen the protein that is being de-immunized for peptides that correspond to (known) self-peptides which should not normally induce a Th response. Though it is not known in detail which endogenous proteins are internalized during T cell maturation and as such give rise to self-peptides, antibodies are among them (Kirschmann et al. 1995 J. Immunol. 155, 5655-5662, Verreck et al. 1996 Immunogenetics 43, 392-397, Harding et al. 2010 MAbs. 2, 256-265).

p75-NTR Fc-Fusion Protein Design

The specific allotype of the Fc portion of the p75-NTR Fc-fusion protein was the IgG pCon vector IgGza (see above).

The design of a p75-NTR Fc-fusion protein proceeded in several stages:

The exact construct of the p75-NTR sequence to be used in the Fc-fusion protein was defined. Several factors were considered including:

The p75-NTR Fc-fusion should be able to bind several neurotrophins including at least NGF, BDNF, NT-3 and NT-4; flexibility must be retained in the p75-NTR Fc-fusion protein.

Unwanted alpha-secretase cleavage sites is present in the extracellular domain on the p75-NTR-Fc (SEQ ID No. 1), these must be removed from the sequence as they will be subjected to cleavage and consequently reduce the biological activity and PK profile of the p75-Fc product in vivo. The original p75-Fc product (see SEQ ID No. 1) contained alpha-secretase cleavage sites and consequently the half life and biological activity (PK/PD) was significantly reduced compared to SEQ ID No. 3 (see below).

Appropriate empirical linkers, suitable for use to join the extracellular p75-NTR domain and the Fc in a p75-NTR Fc-fusion protein, were identified. Linker sequences containing sites that can potentially participate in Post-translational Modification (PTMs) were excluded.

Several variants of the p75-NTR Fc-fusion protein were constructed in silico using the defined p75-NTR construct with the appropriate portion of the Fc region using different potential linker sequences. Structural modelling and analysis of the C-terminus of p75-NTR extracellular domain, Fc hinge region and potential linker was attempted (see Table 1).

The variants with different linker sequences were screened using EPIBASE™ for potential Th epitopes.

The expressed Sequence 3 p75-NTR Fc-fusion protein (SEQ ID No. 3) was proposed on the basis of the predicted immunogenicity risk.

Fc-Fusion Protein Sequence Analysis

The protein sequences for thirteen of the currently available therapeutic Fc-fusion proteins were obtained from the United States Adopted Names (USAN). Where possible the protein sequences were cross referenced and checked against other online resources, such as online patent information websites. Protein sequences for research-grade Fc-fusion proteins were obtained from other commercial suppliers using online resources.

To identify the putative parental sequence that the various Fc-fusion proteins were derived from, the Fc-fusion protein sequences were aligned to the translated protein products of in-house Lonza IgG pCon vectors using MAFFT (Katoh et al. 2002 Nucleic Acids Res. 30, 3059-3066). The aligned Fc-fusion protein sequences were then truncated at the position where the Fc-fusion began to match the IgG sequence. In order to determine where the IgG sequence began a criteria of three consecutive IgG residues was used.

A Blast search (Altschul et al. 1997 Nucleic Acids Res. 25 3389-3402) of an in house copy of the Uniprot database (The UniProt Consortium, UniProt release 2012-09-Oct. 3, 2012) was performed using the truncated Fc-fusion protein sequences without their IgG sequence, to identify the closest matching protein sequences. Each Fc-Fusion protein sequence was then manually re-aligned against both the closest matching sequences found in Uniprot database and the closest matching Lonza IgG pCon sequence. The junctions between the fusion partners and the Fc regions were then extracted and two sets were created, one for the 13 therapeutic Fc-fusion proteins and one for the commercially available Fc-fusion proteins. From these two sets the linker regions were then defined.

The set of commercially available Fc-fusion proteins sequences were then truncated at the N-terminal position where sequence identity to the closest matching Lonza IgG pCon sequence was found. The truncated sequences were then sorted and a non-redundant set of sequences was generated.

EPIBASE™ Immunoprofiling

EPIBASE™ immunoprofiling was performed on the Fe-fusion protein variants using the 85 HLA class II allotypes in the Global set.

A comparison of the Fc-fusion protein variants with respect to their immunogenic risk using only HLA binding predictions is very difficult. This is because several important factors are not considered:

The binding peptide may not be generated by the processing machinery and therefore it would never be exposed as a peptide-HLA complex to Th cells by antigen presenting cells.

The peptide-HLA complex may not be recognised by a Th cell.

Given these considerations, three types of quantitative comparisons can be made using EPIBASE™ Immunoprofiling between variant sequences. Firstly, the number of critical epitopes for each of the DRB1, DRB3/4/5, DQ and DP allotype sets can be compared, with peptides binding to multiple allotypes of the same group counted as one. Such an epitope count shows the number of unique epitopes within each set and the difference between the variants reveals the complete removal or addition of potential Th epitopes.

As many epitopes, especially promiscuous epitopes, bind multiple allotypes, the change in the unique Th epitope count may obscure the actual reduction or increase of the immunogenicity potential between variants. Therefore the second quantitative comparison is at the level of each HLA allotype over all Th epitopes, where a count of the binding peptides per allotype for variants, taken together with the serotype and population frequency allows a comparison at either the serotype or allotype level. Thirdly, an approximate score expressing a worst-case immunogenic risk can be calculated as follows:

score=Σ(Epitope Count×Allotype Frequency)

The multiplicative product for each affected allotype is calculated from the number of epitopes predicted to bind a given allotype, and the allele frequency of the affected allotype. The products are summed for all affected DRB1, DRB3/4/5, DQ and DP allotypes used in the study. It should be noted that the individual allotype scores are not the absolute metric by which to measure immunogenicity risk, as all chosen HLA allotypes (DRB1, DRB3/4/5, DQ and DP) should be taken into account.

Human antibody germline sequences, such as those derived from the Lonza pCon IgG Fc, were not considered to be immunogenic, as they are found in the pool of circulating antibodies presented to the human immune system and can be considered to be self-peptides. Similarly, p75-NTR is not considered to be intrinsically immunogenic as it is expressed naturally in the human body. As a result, critical epitopes resulting from peptides wholly derived from either human antibody germline sequences or from p75-NTR are excluded from the counts and immunogenicity scores presented.

Structural Modelling

Structural models of the proposed p75-NTR Fc-fusion protein, were generated using Lonza's modelling platform. Candidate structural template fragments for the p75-NTR and the Fc portion were scored, ranked and selected from both an in-house antibody database base and the Protein Data Bank (PDB), on their sequence identity, as well as qualitative crystallographic measures of the template structure, such as the resolution (in Ångstrom (Å)).

A sequence alignment of the structural template fragments to the p75-NTR Fc-fusion protein was generated. The template fragments along with the sequence alignment were processed by MODELLER™ (Sali et al. 1993 J. Mol. Biol 234, 779-815). This protocol creates conformational restraints derived from the set of aligned structural templates. An ensemble of structures that satisfy the restraints is created by conjugate gradient and simulated annealing optimization procedures. One or more model structures are selected from this ensemble on the basis of an energy score, derived from the score of the protein structure and satisfaction of the conformational restraints. The models were inspected and the side chains of the positions which differ between the target and template were optimized using a side chain optimization algorithm and energy minimized. A suite of visualization and computational tools were used to assess the conformational variability of the structures, as well as the core and local packing of the domains to select one or more preferred models.

p75-NTR Fc-Fusion Protein Design

Three linker variants of the p75-NTR Fc-fusion proteins were designed. Given the design constraints of attempting to retain flexibility in the p75-NTR regions in the final Fc-fusion proteins and the desire to avoid unwanted cleavage sites for alpha and gamma secretase, the extracellular p75-NTR sequence was truncated at position G237. The original p75NTR-Fc Sequence 1 (SEQ ID No. 1) was truncated at position A250. Alpha secretase cleavage sites have been identified in the extracellular portion of p75-NTR between positions 241-242 and positions 244-245 (Zampieri et al. 2005 J Biol Chem. 280, 14563-71) and a putative gamma secretase cleavage site has been inferred by sequence homology in the regions of position 282. It is evident from the PK/PD of Sequence 1 that the PK and biological activity of Sequence 1 (SEQ ID No. 1) is significantly reduced compared to Sequence 3 (SEQ ID No. 3). It was concluded from these experiments that alpha and gamma secretase sties contributed to the reduction in in vivo activity.

The key requirements of the linkers chosen for the variants are to allow the flexibility of the fusion partner in the Fc-fusion protein, to avoid introducing any residues capable of bearing PTMs and to maintain a low immunogenicity risk.

There are two classes of linkers available to join the p75-NTR to the Fc constant region, empirical linkers and linkers derived from natural proteins. The linkers derived from natural proteins may introduce sites capable of unwanted PTM and due to their nature potentially have a greater risk of introducing immunogenicity. The empirical linkers were taken forward for further investigation for these reasons and can broadly be categorised as either flexible or rigid. The sequences of the repeating unit empirical linkers are listed below, together with their flexibility classification:

$(G_4S)_X$—flexible
$G_X$—flexible
$A(EAAAK)_XA$—rigid (SEQ ID No. 14)
$(PA)_X$—rigid Given the need for flexibility to ensure binding to multiple neurotrophic ligands including at least NGF, BDNF, NT3 and NT4 in the final Fc-fusion protein, only flexible linkers were considered.

Based on these considerations, three variants were constructed, one variant using a poly-glycine linker and two variants using the tetra-glycine serine linker. The variants all consider G209 (expressed protein see Sequence 3 (SEQ ID No. 3)) in the original p75-NTR sequence as part of the linker sequence. In addition the variants contain the cysteine to serine mutation at the location equivalent to position 222 in the original p75-NTR Fc-fusion protein Sequence 1 (SEQ ID No. 1). The linker regions of the variants are shown in FIG. 3.

An analysis of the immunogenicity potential for each of the variants and the other sequences indicated in FIG. 1 was performed using EPIBASE™. The predicted immunogenicity scores for critical epitopes affecting the 85 HLA class II allotypes in the Global set are shown below in, Table 1. Additionally, information about the number of allotypes affected by non-critical epitopes is also shown in Table 1.

TABLE 1

Summary of the critical epitope scores calculated

| Molecule | Critical Epitope Score | | | | Non-critical Epitopes |
|---|---|---|---|---|---|
| | DRB1 | DRB3/4/5 | DQ | DP | |
| Commercial p75-Fc | 167.7 | 53.6 | 0 | 0 | — |
| p75-Fc | 55.1 | 24.2 | 0 | 0 | — |
| p75-Fc (C222S) | 75 | 24.2 | 0 | 0 | — |
| p75-Fc (G4x1) (SEQ ID No. 3) | 0 | 0 | 0 | 0 | 7 medium DQ Epitopes |
| p75-Fc (G4Sx1) | 2.4 | 0 | 0 | 0 | 1 medium DRB1, 5 medium DQ Epitopes |
| p75-Fc (G4Sx2) | 2.4 | 0 | 42.2 | 0 | 3 strong DQ, 1 medium DRB1, 6 medium DQ Epitopes |
| SEQ ID No. 15 | 0 | 0 | 0 | 0 | — |
| Apollo p75NTR-Fc | 167.7 | 53.6 | 0 | 0 | — |

On the basis of the predicted immunogenicity and lack of any sites capable of PTM, Variant 1 (p75_Fc_G4x1) has the best characteristics of the three variants and was produced for in vivo testing.

Affinity of Sequence 1 (SEQ ID No. 1) and Sequence 3 (SEQ ID No. 3) p75NTR-Fc for NGF A Biacore chip was prepared in an experiment in which Protein A was amine coupled to flow cells 1 and 2. Single cycle kinetics of NGF binding to captured p75-Fc were measured.

The binding capacity ($R_{max}$) of a chip surface depends of the immobilised level of the ligand (fusion protein). For a kinetics study an $R_{max}$ of 50-100 RU is advised. By using the molecular weights of the p75-Fc and NGF, a desired immobilisation level for the fusion protein can be calculated.

$$R_{max}=(NGF\ molecular\ weight/fusion\ protein\ molecular\ weight) \times immobilisation\ level \times stoichiometric\ ratio:\ 50=(13,500/102,000) \times immobilisation\ level \times 1.$$

Hence, the immobilisation level required=(102,000/13,500)×50=378 RU Sequence 1 (SEQ ID No. 1) and Sequence 3 (SEQ ID No. 3) p75NTR-Fc and NTR-Fc were immobilised onto the Protein A chip prior to single cycle kinetics.

Using a manual run, Sequence 3 p75-Fc (SEQ ID No. 3) was captured onto flow cell 2 of the Protein A chip until the desired level of approx. 380 RU was achieved. This was performed with a 22 second injection at a flow rate of 10 μl/min and Sequence 3 p75-Fc (SEQ ID No. 3) concentration 10 μg/ml which resulted in 418 RU of the fusion protein captured onto the protein A surface.

In the first instance NGF concentrations of 10, 5 2.5, 1.25 and 0.625 nM were tested. These concentrations were tested as the $K_D$ for the fusion protein was approximated to be within this range of NGF concentrations.

The single cycle kinetics method involved:
injecting 0.625 nM of NGF onto the captured p75-Fc for 120 seconds at 30 μl/min
this process was then repeated with an injection of NGF at 1.25 nM, followed by 2.5, 5 and 10 nM
after the final concentration of NGF had been injected a 600 second dissociation phase was performed by flowing the running buffer (HBS-EP) over the chip.

Once completed the chip was regenerated back to its Protein A surface by injecting 10 mM Glycine HCl, pH 2 for 60 seconds at 30 μl/min.

Sequence 1 (SEQ ID No. 1) p75-Fc was then captured onto the chip by performing a 38 second injection at a flow rate of 10 μl/min at a concentration of 10 μg/ml. This achieved the desired level of 430 RU. The single cycle kinetics procedure described above was then repeated.

Data Analysis

The fusion protein-NGF binding data was analysed in the following manner using the Biacore T200 evaluation software v1:
Data is recorded for the binding of NGF to the fusion protein on flow cell 2 (Fc=2) and for NGF flowing over the control flow cell 1 (Fc=1; protein A alone).
The data from Fc=1 is then subtracted from Fc=2 to give "2-1" binding data.
The 2-1 binding data for an injection of 0 nM (HBS-EP running buffer alone) is then subtracted from all the 2-1 binding data to control for any drifts in baseline throughout the experiment.
Finally, this data is then fitted to a 1:1 binding model to calculate binding characteristics including association rates (ka), dissociation rates (kd) and affinities ($K_D$).

Single Cycle Kinetics Data of NGF Binding to Captured Sequence 1 (SEQ ID No. 1) and 3 (SEQ ID No. 3) p75-Fc Fusion Proteins The binding profiles for both fusion proteins to NGF were 400 pM (SEQ ID No. 1) and 360 pM (SEQ ID No. 3). It was evident from these studies that Sequence 3 (SEQ ID No. 3) had a greater affinity for NGF than Sequence 1 (SEQ ID No. 1).

In Vivo Pharmacokinetics of Sequence 1 (SEQ ID No. 1) and 3 (SEQ ID No. 3) p75NTR-Fc Male Wistar rats (from Charles River UK) weighing 120-150 g on arrival were used in this study. Each animal was checked on arrival and appeared outwardly healthy. They were randomly assigned to a cage of two and each rat was allocated a unique identification number by a tattoo imprinted on the tail. Animals were acclimatised to the animal unit for at least 10 days prior to the start of the study on day 0.

Once the rats had acclimatised to their environment they were transferred to a stock/procedure room, where all the in vivo procedures were carried out. Animals were kept illuminated by fluorescent lights set to give a 12 hour light-dark cycle (on 07.00 off 19.00) as recommended in the Home Office Animals (Scientific Procedures) Act 1986. The rooms were air-conditioned and the air temperature (21° C.+/−2° C.) and relative humidity were routinely measured.

Rats were fed an irradiated diet (Scientific Animal Food and Engineering, Augy, France) and autoclaved water was available ad libitum throughout the study. Each batch of diet was checked and screened routinely for composition and contaminants. Nesting and cages were autoclaved and each cage was individually ventilated (IVC system).

The study design was such that there were 5 treatment groups as outlined in Table 2.

TABLE 2

Treatment Groups

| Rat number | Treatment | Dose | Route of administration | Treatment days | n |
|---|---|---|---|---|---|
| 1-4 | Seq 1p75-Fc | 1 mg/kg | Subcutaneous | 0, 5 and 10 | 4 |
| 5-8 | Seq 2 p75-Fc | 1 mg/kg | Subcutaneous | 0, 5 and 10 | 4 |

A blood sample was taken from the tail vein of rats at approximately the same time (10 am-11.30 am) on day 2, 4, 6, 8, 12 and 15 and plasma prepared.

Blood Sampling from the Tail Vein

Rats were placed in a warming box set at 38° C. for a minimum of five minutes but for no longer than ten minutes to induce vasodilation of the tail vein and facilitate bleeding. Rats were confined in an appropriate sized restrainer, the tail vein was punctured using a sterile 23 G needle and the blood allowed to flow into a CB300 microvette tube (Sarstedt 16.444). A minimum of 100 μl and a maximum of 300 μl of blood were collected from each rat at all time points. A different site was chosen for repeat sampling and the rats were calm throughout the procedure. The rats tolerated repeat blood sampling well with no evidence of bruising. The blood collected was used to prepare plasma.

Terminal Blood Sample from the Heart

Terminal blood samples were taken by cardiac puncture under Isoflurane anaesthetic with a Terumo 1 ml syringe and 23 G needle. Animals were then killed by cervical dislocation. The blood collected was used to prepare serum.

Plasma Preparation

The microvette containing blood from the tail vein was gently inverted several times to ensure good mixing with the anticoagulant (Potassium-EDTA). Tubes were then place on ice prior to being centrifuged at 2700×g for 10 minutes and the plasma aliquoted into polypropylene tubes (two aliquots per animal per time point, except on day 2 when only one aliquot was prepared). All plasma samples were immediately frozen and stored at −80° C. until needed.

Serum Preparation

Blood collected by cardiac puncture on day 15 was allowed to clot in a polypropylene tube at room temperature for between 2 and 3 hours (3 hours maximum). Clotted blood was then centrifuged at 4000×g for 5 minutes and the serum aliquoted into polypropylene tubes (two aliquots per animal). Serum samples were immediately frozen and stored at −80° C.

Determination of Plasma p75NTR-Fc.

Plasma p75NTR-Fc was measured using a modified ELISA for p75NTR (R and D systems) and IgG1 Fc ELISA (R and D systems) as a means of determining intact total plasma concentrations of p75NTR-Fc.

The pharmacokinetics of Sequence 1 (SEQ ID No. 1) and Sequence 3 (SEQ ID No. 3) of p75NTR-Fc were determined.

|  | Sequence 1 p75NTR-Fc (SEQ ID No. 1) | Sequence 3 p75NTR-Fc (SEQ ID No. 3) |
| --- | --- | --- |
| Ligand | NGF BDNF NT3/4 | NGF BDNF NT3/4 |
| MW | 90-120 kDa | 90-100 kDa |
| Kd Biacore | 390 pM | 360 pM |
| Rat $T_{1/2}$ | 1.5 days | 3.3 days |
| Rat $T_{max}$ | 0.5 days | 3 days |
| Pain efficacy | 10 mg/kg | 1-3 mg/kg |
| $C_{eff}$ | 10 nM | 2 nM |

Conclusion

By removing the alpha and gamma secretase cleavage sites of Sequence 1 (SEQ ID No. 1) p75NTR-Fc compared to Sequence 3 (SEQ ID No. 3) this has significantly improved the PK of p75NTR-Fc and subsequently the efficacy as assessed by pain scores following chronic treatment. The alpha and gamma secretase cleavage sites of Sequence 1 (SEQ ID No. 1) p75NTR-Fc made this compound inappropriate as an in vivo drug for the treatment of pain and other pathologies related to neurotrophin biology for example respiratory disease.

Sequence 3 (SEQ ID No. 3) is stable has an improved PK/PD profile compared to Sequence 1 (SEQ ID No. 1) and a greater affinity to neurotrophins.

P75NTR-Fc (SEQ ID No. 3) is Analgesic.

The aim of this study was to investigate the effects of chronic exposure of p75NTR-Fc (SEQ ID No. 3) on pain efficacy in monosodium-iodoacetate (MIA) induced osteoarthritis (OA) in rats.

Previously, we also have shown that an assessment of spontaneous pain could made by measurement of static weight bearing using an incapacitance tester and that this correlated with the histopathology of the knee. Pre-clinical studies using novel therapies for pain have been criticized for their capability to induce bias in the data. To address this, both the left and right knees were randomly chosen for the induction of OA, and all operators of the everyday in vivo tasks were blinded to the status of each knee. Typically from the literature induction of OA is carried out in the right knee only, but in a previous studies we found no consistent differences between the induction of OA in the left versus the right knee regardless of the time point or dose of MIA used.

Preparation of MIA

MIA was prepared at 0.3 mg/50 µl ETF-PBS (the volume used for each intra-articular injection) which is equivalent to 6 mg/ml stock solution. 302 mg of MIA was weighed out and dissolved in 50.3 ml ETF-PBS. The MIA was prepared a day in advance and was stored at 4° C. in the dark until required.

Animals 44 male Wistar rats (from Charles River UK) weighing 110-130 g on arrival were used in this study. Each animal was checked on arrival and appeared outwardly healthy. They were randomly assigned to a cage of two and each rat was allocated a unique identification number by a tattoo on the tail. Animals were acclimatised to the animal unit for at least 10 days prior to the start of the study on day 0. Once the rats had acclimatised to their environment they were transferred to a stock/procedure room, where all the in vivo procedures were carried out. Animals were kept illuminated by fluorescent lights set to give a 12 hour light-dark cycle (on 07.00 off 19.00) as recommended in the Home Office Animals (Scientific Procedures) Act 1986. The rooms were air-conditioned and the air temperature (21° C.+/−2° C.) and relative humidity were routinely measured.

Rats were fed an irradiated diet (Scientific Animal Food and Engineering, Augy, France) and autoclaved water was available ad libitum. Each batch of diet was checked and screened routinely for composition and contaminants. Nesting and cages were autoclaved and each cage was individually ventilated (IVC system).

Experimental Design

The study design was such that there were five groups of animals: control human antibody (n=6), 0.3 mg/kg p75NTR-Fc (SEQ ID No. 3), 1 mg/kg p75NTR-Fc (SEQ ID No. 3), 3 mg/kg p75NTR-Fc (SEQ ID No. 3) and 3 mg/kg PG-007 (biosimilar anti-NGF antibody of the Pfizer Tanezumab).

Antibodies and p75NTR-Fc (SEQ ID No. 3) were administered by subcutaneous injection every 5 days for 25 days.

Body weight was measured and a baseline blood sample was taken from the tail vein in the morning of day −2. At approximately the same time on day −1 baseline static weight bearing was measured. On day 0, again at approximately the same time of day, all rats were treated with their respective antibody or p75NTR-Fc fusion protein. Three hours later all animals were given an intra-articular injection of 0.3 mg MIA into one knee (ETF-PBS was injected into the contralateral knee).

Randomisation of Treatment

Prior to the start of the study rats were weighed and each cage of two rats was randomly assigned to a treatment group so that the mean body weight of animals in each group were approximately equal. In addition to each rat being allocated to a particular treatment group further randomisation was also carried out so that either the left or right knee of each rat was injected with MIA (with the contralateral knee from each rat injected with ETFPBS). The allocation of treatment group and which knee received treatment for each rat was produced using a random number generator in Microsoft Excel for the Mac (Version 14.1.1). Personnel who had no contact with the animals carried out the randomisation procedure and allocation.

Two 7 ml polypropylene vials were labeled for each animal to denote the left or right knee (total of 88 vials). Two people (one scoring and checking to the master randomisation sheet and one aliquoting the solution for the intraarticular injection) prepared the 88 vials. The aliquoting was carried out in sequence so that the MIA vials were filled first followed with the remaining vials being filled with ETF-PBS (this was the contralateral knee vial for each animal). Throughout the study in vivo scientists were blind to the treatment status of all animals.

Animal Procedures

Intra-Articular Injection of the Knee

All rats were anaesthetised by inhalation of Isoflurane using a Boyles Apparatus. The hairs on both knees of each animal were clipped and the knees swabbed with ethanol. Each knee was injected through the infra-patellar ligament with 50 µl of either 0.3 mg MIA in ETF-PBS or ETF-PBS alone using a 0.5 ml sterile Becton Dickinson Micro-Fine insulin syringe with an attached 27 G needle.

Assessment of Spontaneous Pain

Spontaneous pain was determined for each animal by measuring the weight bearing of the left and right hind limbs using an incapacitance tester (Linton Instruments, U.K.). Rats were placed in an appropriately sized perspex animal box on the incapacitance tester so that their hind feet sat on separate sensors. The size of the box allowed the rat to sit comfortably without squashing but similarly did not permit it sufficient space to turn around. Once the rat was steady and calm, the weight bearing of each limb was recorded over 5 seconds and the average force in grams exerted by both hind limbs was recorded. The weight distribution of the hind paws was determined five times (the validity for which we have demonstrated previously) for each rat at each time point, and the mean of the five readings calculated. The individual weight bearing data was converted into a weight distribution by dividing the weight of the right limb by the total weight for both hind limbs.

Spontaneous Pain Measurements Following MIA-Induced OA

Spontaneous pain was assessed using an incapacitance tester to measure the distribution of weight through the rear limbs. Assessments were carried out at baseline and at 3 weeks post-treatment with MIA.

Data is shown in FIG. 4 is illustrated as the proportion of the total weight over the rear limbs.

For naïve animals, there was no statistically significant difference between the proportion of weight on the rear limbs and the theoretical expectation of 0.5.

For the animals treated with control antibodies, there was statistically significantly less weight being put on the treated limb than on the untreated limb (39% vs. 61%). In animals treated with the anti-NGF antibody (PG-007 Tanezumab biosimilar 3 mg/kg) and those treated with p75NTR-Fc (SEQ ID No. 3) at 0.3 and 1 mg/kg there was no statistically (P<01) significant difference between the proportion of weight on the treated rear limb and the theoretical expectation of 0.5 (even distribution across both rear limbs) at any of the time points measured. The analgesic effect of p75NTR-Fc (SEQ ID No. 3) at 3 mg/kg was even more statistically significant (P<0.05) compared to corresponding controls.

It is evident from these studies that p75NTR-Fc (SEQ ID No. 3) is analgesic in the MIA rat model of OA. The analgesic effects p75NTR-Fc (SEQ ID No. 3) were greater that observed for anti-NGF antibodies (PG-007: biosimilar Pfizer anti-NGF antibody Tanezumab) at similar doses: 3 mg/kg subcutaneous.

Unexpected Improvement in Affinity of p75NTR-Fc Molecule Sequence 3 and Sequence 15 Against Individual Neurotrophins It is generally accepted from the literature and prior art that the low affinity p75 neurotrophin receptor and has a similar affinity for all the neurotrophins of around 1 nM (Ichim et al., 2012 Exp Cell Res 318(11): 1221-8). Furthermore the prior art of Apollo Life Sciences (Molecules and chimeric molecules thereof US 20090232808 A1) further exemplifies the similarity of the affinity of p75 neurotrophin receptor for the individual neurotrophins. "NGFR is a type I membrane protein that is synthesised as a 427 amino acid glycoprotein consisting of a 28 amino acid signal peptide. NGFR binds with equal affinity all neurotrophins".

From Biacore plasma resonance studies we have shown significant changes in the binding affinities of Sequences 3 and 15 coupled to the human IgG1 Fc using GGG linker spacer.

TABLE 3

Biacore Affinity of Sequence 3 and 15 for each neurotrophin

| Sequence | NT-3 (pM) | NT-4 (pM) | BDNF (pM) | NGF (pM) |
|----------|-----------|-----------|-----------|----------|
| 3        | 14        | 181       | 48        | 525      |
| 15       | 15        | 164       | 38        | 498      |

Reducing the Isoelectric Point (pI):

The isoelectric point of Sequences 3 and those disclosed in the Apollo Life Science prior art have theoretical pI of 4.11 however, both these molecules are significantly glycosylated leading to actually pI in the range of 3-4.

Sequence 15 has a theoretical pI of 4.23 and is less glycosylated than other p75NTRs. Subsequently, the pI is in the range of 4-5. This provides a significant advantage (improved formulation and less variability in molecular structure due to variation in glycosylation sites and amount of glycosylation) over Sequence 3 and the sequences disclosed previously in the Apollo Life Science prior art.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A fusion protein comprising the amino acid sequence set forth in SEQ ID NO. 3.

2. The fusion protein according to claim 1, wherein the fusion protein binds to any of NGF, BDNF, NT3 or NT4/5 with a binding affinity ($K_d$) of between about 0.01 nM to about 50 nM as measured by surface plasmon resonance at 20° C.

3. A pharmaceutical composition, comprising the fusion protein according to claim 1 and a pharmaceutically acceptable carrier or excipient, or a combination thereof.

4. A method of treating symptoms of pain in an individual in need thereof comprising administering to said individual a therapeutically effective amount of the fusion protein according to claim 1.

5. A fusion protein comprising the amino acid sequence set forth in SEQ ID NO. 15.

6. A pharmaceutical composition, comprising the fusion protein according to claim 5 and a pharmaceutically acceptable carrier or excipient, or a combination thereof.

7. A method of treating symptoms of pain in an individual in need thereof comprising administering to said individual a therapeutically effective amount of the fusion protein according to claim 5.

\* \* \* \* \*